(12) United States Patent
Pinard et al.

(10) Patent No.: US 8,605,971 B2
(45) Date of Patent: Dec. 10, 2013

(54) METHOD AND SYSTEM FOR DETERMINING AN OPTIMAL DILUTION OF A REAGENT

(75) Inventors: Robert Pinard, New Haven, CT (US); Gregory R. Tedeschi, Cromwell, CT (US); Mark Gustavson, Niantic, CT (US)

(73) Assignee: HistoRx, Inc., New Haven, CT (US)

( * ) Notice: Subject to any disclaimer, the term of this patent is extended or adjusted under 35 U.S.C. 154(b) by 0 days.

(21) Appl. No.: 13/366,081

(22) Filed: Feb. 3, 2012

(65) Prior Publication Data

US 2012/0201435 A1 Aug. 9, 2012

Related U.S. Application Data

(63) Continuation of application No. 12/188,133, filed on Aug. 7, 2008, now Pat. No. 8,121,365.

(60) Provisional application No. 61/190,033, filed on Aug. 7, 2007.

(51) Int. Cl.
*G06K 9/00* (2006.01)

(52) U.S. Cl.
USPC .......................................... 382/128; 382/133

(58) Field of Classification Search
USPC ................................................ 382/128, 133
See application file for complete search history.

(56) References Cited

U.S. PATENT DOCUMENTS

| | | | |
|---|---|---|---|
| 6,458,585 B1 * | 10/2002 | Vachula et al. | 435/325 |
| 7,219,016 B2 * | 5/2007 | Rimm et al. | 702/19 |
| 7,907,271 B2 | 3/2011 | Christiansen et al. | |
| 7,941,275 B2 | 5/2011 | Gholap et al. | |
| 7,978,258 B2 | 7/2011 | Christiansen et al. | |
| 8,121,365 B2 | 2/2012 | Pinard et al. | |
| 8,160,348 B2 | 4/2012 | Pinard et al. | |
| 8,335,360 B2 | 12/2012 | Christiansen et al. | |
| 2004/0014165 A1 * | 1/2004 | Keidar et al. | 435/40.5 |
| 2005/0282179 A1 | 12/2005 | Martin et al. | |
| 2006/0127956 A1 * | 6/2006 | Sompuram et al. | 435/7.2 |
| 2006/0275844 A1 | 12/2006 | Linke et al. | |
| 2009/0034823 A1 * | 2/2009 | Christiansen et al. | 382/133 |

OTHER PUBLICATIONS

Final Office Action mailed Mar. 5, 2013 in U.S. Appl. No. 12/560,129.

(Continued)

*Primary Examiner* — Clayton E Laballe
*Assistant Examiner* — Noam Reisner
(74) *Attorney, Agent, or Firm* — Gilberto M. Villacorta; Daniel Shelton; Foley & Lardner LLP

(57) ABSTRACT

A system and method for automatically and quantitatively determining the optimal dilution of a reagent is provided. In one embodiment, a plurality of dilution sets are received, where each of the dilution sets consist of a different respective dilution value and a respective plurality of immunoassay staining intensity values. A respective dynamic range metric is determining for each of the plurality of dilution sets relative to the respective plurality immunoassay staining intensity values. Having found the respective dynamic range metric, a dilution set having the numerically optimal dynamic range metric is selected and the dilution value of that dilution set is selected as being representative of an optimal dilution level of the reagent for use in a quantitative immunoassay. In one embodiment, a system is provided with a microscope, an image sensor, and processor module configured determine an optimal dilution of a reagent for use in an quantitative immunoassay.

11 Claims, 18 Drawing Sheets

(56) References Cited

OTHER PUBLICATIONS

Notice of Reasons for Rejection mailed Feb. 19, 2013 in Japan Appln. No. 2011-527047, with translation.
Butler "Enzyme-Linked Immunosorbent Assay," Journal of Immunoassay, vol. 21(2&3), 2000, pp. 165-209.
Camp et al., "Quantitative Analysis of Breast Cancer Tissue Microarrays Shows That Both High and Normal Levels of HER2 Expression are Associated with Poor Outcome," Cancer Research, vol. 63, Apr. 2003, pp. 1445-1448.
Camp et al., "X-Tile: A New Bio-Informatics Tool for Biomarker Assessment and Outcome-Based Cut-Point Optimization," Clinical Cancer Research, vol. 10, 2004, pp. 7252-7259.
Camp et al., "Automated Subcellular Localization and Quantification of Protein Expression in Tissue Microarrays," New Technology—Nature Medicine, 2002, vol. 8, No. 11, pp. 1323-1327.
Dell'Anna et al., "An Automated Procedure to Properly Handle Digital Images in Large Scale Tissue Micorarray Experiments", Computer Methods and Programs in Biomedicine, Elsevier, Amsterdam, NL, vol. 79, No. 3, Sep. 1, 2005, pp. 197-208.
Dolled-Filhart et al., "Quantitative In Situ Analysis of B-Catenin Expression in Breast Cancer Shows Decreased Expression is Associated with Poor Outcome," Cancer Res., vol. 66, No. 10, 2006, pp. 5487-5494.
Elias, "Immunoshistopathology a Practical Approach to Diagnosis," American Society of Clinical Pathologists, ASCP Press, Chicago, 1990. (Table of Contents).
Gustavson, et al., Mark D., "Development of an Unsupervised Pixel-Based Clustering Algorithm for Compartmentalization of Immunohistochemical Expression Using Automated Quantitative Analysis", Applied Immunohistochemistry, vol. 17, No. 4, Jul. 1, 2009, pp. 329-337.
Harvey et al., "Estrogen Receptor Status by Immunohistochemistry is Superior to the Ligand-Binding Assay for Predicting Response to Adjuvant Endocrine Therapy in Breast Cancer," Journal of Clinical Oncology, vol. 17, No. 5, 1999, pp. 1474-1481.
International Search Report and Written Opinion, PCT/US2009/056996, Jan. 25, 2010, 11 pgs.
Jain, "Fundamentals of Digital Image Processing", Image Analysis and Computer Vision, Chapter 9, Jan. 1, 1989, p. 418.
Jowett, "Tissue In Situ Hybridization: Methods in Animal Development," John Wiley & Sons, Inc. and Spektrum Akademischer Verlag, 1997 (Table of Contents).
Kallioniemi et al., "Tissue Microarray Technology for High-Throughput Molecular Profiling of Cancer," Human Molecular Genetics, vol. 10, No. 7, 2001, pp. 657-662.
Kononen et al., "Tissue Microarrays for High-Throughput Molecular Profiling of Tumor Specimens," Nature Medicine, vol. 4, No. 7, Jul. 1998, pp. 844-847.
Leitch, "In Situ Hybridization: A Practical Guide," Oxford BIOS Scientific Publishers, Microscopy Handbooks (1994)—Table of Contents.
Lillie, R. D. "H.J. Conn's Biological Stains: A Handbook on the Nature and Uses of the Dyes Employed in the Biological Laboratory," The Williams & Wilkins Company, copyright 1969, Eighth Edition.
McCabe et al., "Automated Quantitative Analysis (AQUA) of In Situ Protein Expression, Antibody Concentration, and Prognosis," Journal of the National Cancer Institute, vol. 97, No. 24, pp. 1808-1815, Dec. 21, 2005.
McGinty et al., "Double Immunostaining Reveals Distinctions Among Opioid Peptidergic Neurons in the Medical Basal Hypothalamus," Brain Research, vol. 278, pp. 145-153, 1983, Elsevier.
Office Action in CN Appln No. 200980137750.0 dated Oct. 25, 2012.
Paik et al., "Benefit from Adjuvant Trastuzumab May Not Be Confined to Patients With IHC 3 and/or FISH Positive Tumors: Central Testing Results from NSABP B-31," vol. 25, 2007, pp. 511.
Perez et al., "HER2 Testing by Local, Central, and Reference Laboratories in Specimens from the North Central Cancer Treatment Group N9831 Intergroup Adjuvant Trial", Journal of Clinical Oncology, vol. 24, 2006, pp. 3032-3038.
Raeside, et al., "Monte Carlo Principles and Application," Phs Med Biol., vol. 21, No. 2, 1976, pp. 181-197.
Rimm et al., "Tissue Microarray: A New Technology for Amplification of Tissue Resources," The Cancer Journal, vol. 7, No. 1, Jan./Feb. 2001, pp. 24-31.
Rubin et al. "Quantitative determination of expression of the prostate cancer protein alpha-methylacyl-CoA racemase using automated quantitative analysis (AQUA): A novel paradigm for automated and continuous biomarker measurements," American Journal of Pathology, vol. 164, No. 3, Mar. 2004, pp. 831-840.
Sambrook et al., "Molecular Cloning, a Laboratory Manual," 1989, Cold Spring Harbor Laboratory Press, Cold Spring Harbor, N.Y., 30 pages.
Schweitzer et al. "Multiplexed protein profiling on microarrays by rolling-circle amplification," Nature Biotechnology, vol. 20, 2002, pp. 359-365.
Search Report mailed Nov. 18, 2008 in International Appln. No. PCT/US2008/09454.
Teverovskiy, et al.,"Automated Localization and Quantificiation of Protein Multiplexes Via Multispectral Fluorescence Imaging", Biomedical Imaging: From Nano to Macro, 2008, ISBI 2008, 5th IEEE International Symposium on, IEEE, Piscataway, NJ, May 14, 2008, pp. 300-303.
Wolff, et al., Arch Pathol Lab Med., "American Society of Clinical Oncology/College of American Pathologists Guideline Recommendations for Human Epidermal Growth Factor Receptor 2 Testing in Breast Cancer," vol. 131, Jan. 2007, p. 18-43.

\* cited by examiner

CORRELATIONS

| | | LOG_25 | LOG_50 | LOG_100 | LOG_250 | LOG_1000 |
|---|---|---|---|---|---|---|
| LOG_25 | Pearson Correlation | 1 | .911** | .829** | .780** | .667** |
| | Sig. (2-tailed) | | .000 | .000 | .000 | .000 |
| | N | 30 | 30 | 30 | 30 | 30 |
| LOG_50 | Pearson Correlation | .911** | 1 | .866** | .875** | .737** |
| | Sig. (2-tailed) | .000 | | .000 | .000 | .000 |
| | N | 30 | 30 | 30 | 30 | 30 |
| LOG_100 | Pearson Correlation | .829** | .866** | 1 | .956** | .908** |
| | Sig. (2-tailed) | .000 | .000 | | .000 | .000 |
| | N | 30 | 30 | 30 | 30 | 30 |
| LOG_250 | Pearson Correlation | .780** | .875** | .956** | 1 | .906** |
| | Sig. (2-tailed) | .000 | .000 | .000 | | .000 |
| | N | 30 | 30 | 30 | 30 | 30 |
| LOG_1000 | Pearson Correlation | .667** | .737** | .908** | .906** | 1 |
| | Sig. (2-tailed) | .000 | .000 | .000 | .000 | |
| | N | 30 | 30 | 30 | 30 | 30 |

**. CORRELATION IS SIGNIFICANT AT THE 0.01 LEVEL (2-TAILED).

FIG. 10

CORRELATIONS

| | Spearman's rho | LOG_25 | LOG_50 | LOG_100 | LOG_250 | LOG_1000 |
|---|---|---|---|---|---|---|
| LOG_25 | Correlation Coefficient | 1.000 | .930** | .865** | .863** | .733** |
| | Sig. (2-tailed) | . | .000 | .000 | .000 | .000 |
| | N | 30 | 30 | 30 | 30 | 30 |
| LOG_50 | Correlation Coefficient | .930** | 1.000 | .860** | .911** | .704** |
| | Sig. (2-tailed) | .000 | . | .000 | .000 | .000 |
| | N | 30 | 30 | 30 | 30 | 30 |
| LOG_100 | Correlation Coefficient | .865** | .860** | 1.000 | .956** | .879** |
| | Sig. (2-tailed) | .000 | .000 | . | .000 | .000 |
| | N | 30 | 30 | 30 | 30 | 30 |
| LOG_250 | Correlation Coefficient | .863** | .911** | .956** | 1.000 | .844** |
| | Sig. (2-tailed) | .000 | .000 | .000 | . | .000 |
| | N | 30 | 30 | 30 | 30 | 30 |
| LOG_1000 | Correlation Coefficient | .733** | .704** | .879** | .844** | 1.000 |
| | Sig. (2-tailed) | .000 | .000 | .000 | .000 | . |
| | N | 30 | 30 | 30 | 30 | 30 |

**. CORRELATION IS SIGNIFICANT AT THE 0.01 LEVEL (2-TAILED).

FIG. 11

CORRELATIONS

| | | Log2_25 | Log2_50 | Log2_100 | Log_250 | Log_1000 |
|---|---|---|---|---|---|---|
| Log2_25 | Pearson Correlation | 1 | .994** | .995** | .959** | .880** |
| | Sig. (2-tailed) | | .000 | .000 | .000 | .000 |
| | N | 34 | 34 | 34 | 34 | 34 |
| Log2_50 | Pearson Correlation | .994** | 1 | .995** | .967** | .903** |
| | Sig. (2-tailed) | .000 | | .000 | .000 | .000 |
| | N | 34 | 34 | 34 | 34 | 34 |
| Log2_100 | Pearson Correlation | .995** | .995** | 1 | .973** | .900** |
| | Sig. (2-tailed) | .000 | .000 | | .000 | .000 |
| | N | 34 | 34 | 34 | 34 | 34 |
| Log_250 | Pearson Correlation | .959** | .967** | .973** | 1 | .933** |
| | Sig. (2-tailed) | .000 | .000 | .000 | | .000 |
| | N | 34 | 34 | 34 | 34 | 34 |
| Log_1000 | Pearson Correlation | .880** | .903** | .900** | .933** | 1 |
| | Sig. (2-tailed) | .000 | .000 | .000 | .000 | |
| | N | 34 | 34 | 34 | 34 | 34 |

**.CORRELATION IS SIGNIFICANT AT THE 0.01 LEVEL (2-TAILED).

*FIG. 12*

CORRELATIONS

| Spearman's rho | | Log2_25 | Log2_50 | Log2_100 | Log_250 | Log_1000 |
|---|---|---|---|---|---|---|
| Log2_25 | Correlation Coefficient | 1.000 | .980** | .980** | .955** | .900** |
| | Sig. (2-tailed) | . | .000 | .000 | .000 | .000 |
| | N | 34 | 34 | 34 | 34 | 34 |
| Log2_50 | Correlation Coefficient | .980** | 1.000 | .987** | .975** | .939** |
| | Sig. (2-tailed) | .000 | . | .000 | .000 | .000 |
| | N | 34 | 34 | 34 | 34 | 34 |
| Log2_100 | Correlation Coefficient | .980** | .987** | 1.000 | .965** | .913** |
| | Sig. (2-tailed) | .000 | .000 | . | .000 | .000 |
| | N | 34 | 34 | 34 | 34 | 34 |
| Log_250 | Correlation Coefficient | .955** | .975** | .965** | 1.000 | .948** |
| | Sig. (2-tailed) | .000 | .000 | .000 | . | .000 |
| | N | 34 | 34 | 34 | 34 | 34 |
| Log_1000 | Correlation Coefficient | .900** | .939** | .913** | .948** | 1.000 |
| | Sig. (2-tailed) | .000 | .000 | .000 | .000 | . |
| | N | 34 | 34 | 34 | 34 | 34 |

**.CORRELATION IS SIGNIFICANT AT THE 0.01 LEVEL (2-TAILED).

*FIG. 13*

|  | LOG 25 | LOG 50 | LOG 100 | LOG 250 | LOG 1000 | BEST TITER |
|---|---|---|---|---|---|---|
| STANDARD DEVIATION | 1.01 | 1.05 | 0.87 | 0.77 | 0.54 | 1:50 |
| VARIANCE | 1.027 | 1.102 | 0.750 | 0.591 | 0.295 | 1:50 |
| SKEWNESS | -0.442 | 0.235 | 0.276 | 0.974 | 0.9168.03 | |
| MINIMUM | 8.03 | 6.96 | 3.86 | 3.69 | 2.24 | |
| MAXIMUM | 10.04 | 8.96 | 5.78 | 5.35 | 3.34 | |
| SWING RATIO | 1.25 | 1.28 | 1.50 | 1.45 | 1.49 | 1:100 |
| TOTAL | 3.29 | 3.43 | 3.12 | 2.81 | 2.32 | 1:50 |

*FIG. 14*

Statistics

|  |  | LOG_25 | LOG_50 | LOG_100 | LOG_250 | LOG_1000 |
|---|---|---|---|---|---|---|
| N | Valid | 30 | 30 | 30 | 30 | 30 |
|  | Missing | 0 | 0 | 0 | 0 | 0 |
| Mean |  | 9.02900622317109 | 8.0599052256015 | 4.83339316217483 | 4.38665292681654 | 2.7608084490426 |
| Std. Error of Mean |  | .185065979967931 | .19168754258240 | .158093283142940 | .140342329156046 | .09915826168827 |
| Median |  | 8.95025528650583 | 7.8451831170478 | 4.79296063008228 | 4.26329268110061 | 2.6567077824696 |
| Std. Deviation |  | .013648118552349 | 1.0499159106511 | .865912573674395 | .768686594526777 | .54311216689667 |
| Variance |  | 1.027 | 1.102 | .750 | .591 | .295 |
| Skewness |  | -.442 | .235 | .276 | .974 | .916 |
| Std. Error of Skewness |  | .427 | .427 | .427 | .427 | .427 |
| Range |  | 4.278728158901 | 3.998075581867 | 3.451538461765 | 3.281075316745 | 2.52914925741 |
| Minimum |  | 6.451572595696 | 6.008471366671 | 3.337407531998 | 3.242759512601 | 1.81940047947 |
| Maximum |  | 10.730300754597 | 10.006548948538 | 6.788945993763 | 6.523834829346 | 4.34854973688 |
| Percentiles | 16.66666667 | 8.02772091269092 | 6.9646375776033 | 3.85876821757041 | 3.69296134211289 | 2.2413656244286 |
|  | 33.33333333 | 8.57351465847854 | 7.4955334917615 | 4.40969545750283 | 3.98076572904212 | 2.5386170578081 |
|  | 50 | 8.95025528650583 | 7.8451831170478 | 4.79296063008228 | 4.26329268110061 | 2.6567077824696 |
|  | 66.66666667 | 9.66798357377001 | 8.6786658666386 | 5.19066580317001 | 4.45207920362520 | 2.8651155790381 |
|  | 83.33333333 | 0.04134660555240 | 8.9588164569467 | 5.78123890635526 | 5.34906518952446 | 3.3443078512049 |

*FIG. 15*

|  | LOG 25 | LOG 50 | LOG 100 | LOG 250 | LOG 1000 | BEST TITER |
|---|---|---|---|---|---|---|
| STANDARD DEVIATION | 1.31 | 1.30 | 1.40 | 1.49 | 0.89 | 1:250 |
| VARIANCE | 1.711 | 1.69 | 1.968 | 2.221 | 0.786 | 1:250 |
| SKEWNESS | -0.918 | -0.557 | -0.675 | -0.387 | 0.585 |  |
| MINIMUM | 6.90 | 6.77 | 6.44 | 4.67 | 2.63 |  |
| MAXIMUM | 9.56 | 9.63 | 9.57 | 7.69 | 4.25 |  |
| SWING RATIO | 1.39 | 1.42 | 1.49 | 1.65 | 1.61 | 1:250 |
| TOTAL | 4.41 | 4.41 | 4.86 | 5.36 | 3.29 | 1:250 |

*FIG. 16*

Statistics

|  |  | Log2_25 | Log2_50 | Log2_100 | Log_250 | Log_1000 |
|---|---|---|---|---|---|---|
| N | Valid | 32 | 32 | 32 | 32 | 32 |
|  | Missing | 0 | 0 | 0 | 0 | 0 |
| Mean |  | 8.36254129274469 | 8.2996325846988 | 8.19254863417653 | 6.3554137215105 | 3.4670884523857 |
| Std. Error of Mean |  | .231216974286399 | .22979069226769 | .248006353406112 | .26345784005463 | .15673714453212 |
| Median |  | 8.51820407617593 | 8.3522973792675 | 8.27354822683291 | 6.5591842600166 | 3.5034049034574 |
| Std. Deviation |  | 1.3079607235468 | 1.29989245404826 | 1.402935794166474 | 1.4903426020751 | .88663918209982 |
| Variance |  | 1.711 | 1.690 | 1.968 | 2.221 | .786 |
| Skewness |  | -.918 | -.557 | -.675 | -.387 | .585 |
| Std. Error of Skewness |  | .414 | .414 | .414 | .414 | .414 |
| Range |  | 5.640396220242 | 5.36006733949 | 5.910946475162 | 6.683474984163 | 4.16318128628 |
| Minimum |  | 4.788782543310 | 5.28050020873 | 4.706741139149 | 2.861352467500 | 1.62804987824 |
| Maximum |  | 10.429178783552 | 10.64056754822 | 10.617887614311 | 9.544827451663 | 5.79123116452 |
| Percentiles | 16.66666667 | 6.89841352590684 | 6.7655777745948 | 6.43846192397839 | 4.6731956271822 | 2.6310565866118 |
|  | 33.33333333 | 7.91635877113910 | 7.9511696161292 | 7.66600365851401 | 5.9982918894316 | 3.0582350511652 |
|  | 50 | 8.51820407617593 | 8.3522973792675 | 8.27354822683291 | 6.5591842600166 | 3.5034049034574 |
|  | 66.66666667 | 9.35660698188591 | 9.1182131674341 | 9.02971943280838 | 7.1075839385985 | 3.7227813751616 |
|  | 83.33333333 | 9.55670392634733 | 9.6343745964397 | 9.56598428708468 | 7.69008168862099 | 4.2457595068825 |

*FIG. 17*

METHOD AND SYSTEM FOR DETERMINING AN OPTIMAL DILUTION OF A REAGENT

CROSS-REFERENCE TO RELATED APPLICATIONS

This application is a continuation of U.S. patent application Ser. No. 12/188,133 filed Aug. 7, 2008, which claims priority to Canadian Patent Application. No. 2,596,204 filed Aug. 7, 2007, and U.S. Provisional Patent Application No. 61/190,033, filed Aug. 7, 2007, the entire contents of which are hereby incorporated by reference.

BACKGROUND OF THE INVENTION

The present invention relates generally to the field of biological tissue analysis. More specifically, the present invention relates to a system and method for determining an optimal dilution of a reagent for use in a quantitative immunoassay. There are a variety of different immunoassays for which the claimed invention is applicable including but not limited to tissue-based immunohistochemical, cell-based immunohistochemical analysis such as flow cytometry, and high content screening (HCS) immunohistochemical analysis, enzyme linked immunosorbent assay (ELISA), and western blot assays.

The determination of optimal dilutions of a reagent for a given biological specimen is beneficial to quantitative immunoassays. By way of example, if a reagent is not concentrated enough, then the analysis with the reagent is likely to produce under-detection along with loss of sensitivity at the upper range of the assay. Correspondingly, if the reagent is too concentrated, the reagent is likely to produce over-detection along with loss of sensitivity in the lower range of the assay.

Existing approaches for determining an optimal dilution of a reagent are purely qualitative. The qualitative nature of such an optimization considerably reduces reproducibility of a particular dilution and analysis. Further, such qualitative approach fails to account for a variety of pertinent factors causing reduced reliability of results obtained utilizing such a qualitative optimization.

Immunohistochemistry (IHC) is an immunoassay method for detection of analytes in tissue sections. Traditional IHC assay results have been qualitative in nature, often done by a manual visual assessment through a microscope using a subjective scoring system to indicate a relative amount of analyte present in the tissue sample. In contrast, quantitative IHC analytically measures the amount of one or more analytes of interest in a tissue section. Analytical systems have been developed for quantitative IHC analysis. For example one such system is the AQUA® technology described in U.S. Pat. No. 7,219,016 and in an article entitled "Automated Subcellular Localization and Quantification of Protein Expression in Tissue Microarrays," Camp et al. 2002 Nature Medicine 8(11)1323-1327. However, even with the introduction of such quantitative analysis for IHC, typically preliminary assays are run to determine optimal concentrations of reagents to be used in the analytical assay and these results are assessed qualitatively, not quantitatively. There is a need for methods for quantitatively determining optimal reagent concentrations for use in quantitative immunoassays, including IHC.

SUMMARY OF THE INVENTION

The present invention addresses the above-identified considerations by quantitatively determining an optimal dilution of a reagent for use in quantitative immunoassays. In one embodiment, multiple dilution sets are received, where each of the dilution sets consist of a different respective dilution value and a respective arrangement of immunoassay staining intensity values. A respective dynamic range metric is determined for each of the multiple dilution sets relative to the respective arrangement of immunoassay staining intensity values. Having found the respective dynamic range metric, a dilution set having the numerically optimal dynamic range metric is selected and the dilution value of that dilution set is selected as being representative of an optimal dilution level of the reagent for use in a quantitative immunoassay.

In another embodiment of the present invention, a system for determining an optimal dilution of a reagent for use in a quantitative immunoassay has means for the reception of multiple dilution sets, where each of the dilution sets consist of a different respective dilution value and representative arrangement of immunoassay staining intensity values. Further, the system has means for determining a respective dynamic range metric for each of the multiple dilution sets relative to the respective arrangement of immunoassay staining intensity values. The system is configured with a means for identifying a dilution value which is representative of an optimal dilution value for use in the quantitative immunoassay from the dilution set have the numerically optimal dynamic range metric.

According to another embodiment of the present invention, a system for determining an optimal dilution of a reagent for use in a quantitative immunoassay has an optical microscope configured to magnify at least a portion of a slide-mounted tissue sample as well as an image sensor which is in optical communication with the microscope such that the image sensor is configured to obtain a digitized image of the magnified portion of the slide-mounted tissue sample. The system is also equipped with a processor module in communication with the image sensor. The processor is configured to (i) automatically receive multiple dilution sets, each dilution set having a different respective dilution value and comprising a respective arrangement of immunoassay staining intensity values, (ii) determine for each of the multiple dilution sets a respective dynamic range metric related to the respective one of the plurality of immunoassay staining intensity values, and (iii) identify the dilution set having the numerically optimal dynamic range metric, the dilution value of the identified dilution set being representative of an optimal dilution level of the reagent for use in the quantitative immunoassay.

According to yet another embodiment of the present invention, a computer readable medium is loaded with computer readable instructions for execution by a processor for the purpose of performing a method for determining an optimal dilution of a reagent for use in a quantitative immunoassay. In that method, multiple dilution sets are received, where each of the dilution sets consists of a different respective dilution value and a respective arrangement of immunoassay staining intensity values. A respective dynamic range metric is determined for each of the multiple dilution sets relative to the respective arrangement of immunoassay staining intensity values. Having found the respective dynamic range metric, a dilution set having the numerically optimal dynamic range metric is selected and the dilution value of that dilution set is selected as being representative of an optimal dilution level of the reagent for use in a quantitative immunoassay.

In another embodiment of the present invention, an electromagnetic signal carries computer-readable instructions for determining an optimal dilution of a reagent for use in a quantitative immunoassay. The instructions are such that multiple dilution sets are received, where each of the dilution sets consist of a different respective dilution value and a respective arrangement of immunoassay staining intensity values. A respective dynamic range metric is determined for each of the multiple dilution sets relative to the respective arrangement of immunoassay staining intensity values. Having found the respective dynamic range metric, a dilution set having the numerically optimal dynamic range metric is selected and the dilution value of that dilution set is selected as being representative of an optimal dilution level of the reagent for use in a quantitative immunoassay.

In another embodiment of the present invention, a process for identifying an optimal antibody titer for an immunoassay includes receiving pixelized images of multiple tissue sample sets. Each tissue sample set includes a multiple different tissue samples prepared with respective titer dilution, such that different tissue sample sets have different respective titer dilutions. A quantitative analysis is performed of the pixelized images of the multiple tissue sample sets. This analysis results in a respective selectivity value indicative of a staining intensity of each of the different tissue samples of each of the plurality of tissue sample sets. A respective sensitivity value is determined for each tissue sample set of the multiple tissue sample sets. The respective sensitivity value is determined from pixel intensities of the pixelized images of each of the different tissue samples of each of the multiple tissue sample sets. The process also includes identifying from the respective selectivity values and the respective sensitivity values of each of the plurality of tissue sample sets an optimal titer dilution.

In still another embodiment of the present invention, a system for identifying an optimal antibody titer for an immunoassay includes a computer readable memory configured to receive pixelized images of multiple tissue sample sets. Each tissue sample set includes more than one different tissue samples prepared with a respective titer dilution. Different tissue sample sets have different titer dilutions. The system also includes an image processor in communication with the computer readable memory. The image processor is configured to perform a quantitative analysis of the pixelized images of the multiple tissue sample sets. This results in a respective selectivity value indicative of a staining intensity of each of the different tissue samples of each of the multiple tissue sample sets. The image processor is also configured to perform a determination from pixel intensities of the pixelized images of each of the different tissue samples of each of the multiple tissue sample sets, a respective sensitivity value, and to identify an optimal titer dilution from the respective selectivity values and the respective sensitivity values of each of the plurality of tissue sample sets an optimal titer dilution.

It is to be understood that both the foregoing general description and the following detailed description are exemplary and explanatory only, and are not restrictive of the invention as claimed. These and other features, aspects and advantages of the present invention will become apparent from the following description, appended claims, and the accompanying exemplary embodiments shown in the drawings, which are briefly described below.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 10 is a table illustrating utilization of a parametric Pearson regression to examine data according to one embodiment of the present invention.

FIG. 11 is a table illustrating utilization of a non-parametric Spearman regression to examine data according to one embodiment of the present invention.

FIG. 12 is a table illustrating utilization of a parametric Pearson regression to examine data according to one embodiment of the present invention.

FIG. 13 is a table illustrating utilization of a non-parametric Spearman regression to examine data according to one embodiment of the present invention.

FIG. 14 is a table illustrating a combination of numerical factors to determine an optimal dilution for a reagent for use in a quantitative immunoassay according to an embodiment of the present invention.

FIG. 15 is a table illustrating additional exemplary data used in calculating the factors shown in FIG. 14.

FIG. 16 is a table illustrating a combination of numerical factors for determining an optimal dilution for a reagent for use in a quantitative immunoassay according to an embodiment of the present invention.

FIG. 17 is a table illustrating additional exemplary data used in calculating the factors shown in FIG. 16.

DETAILED DESCRIPTION OF THE PREFERRED EMBODIMENTS

Figure 1:
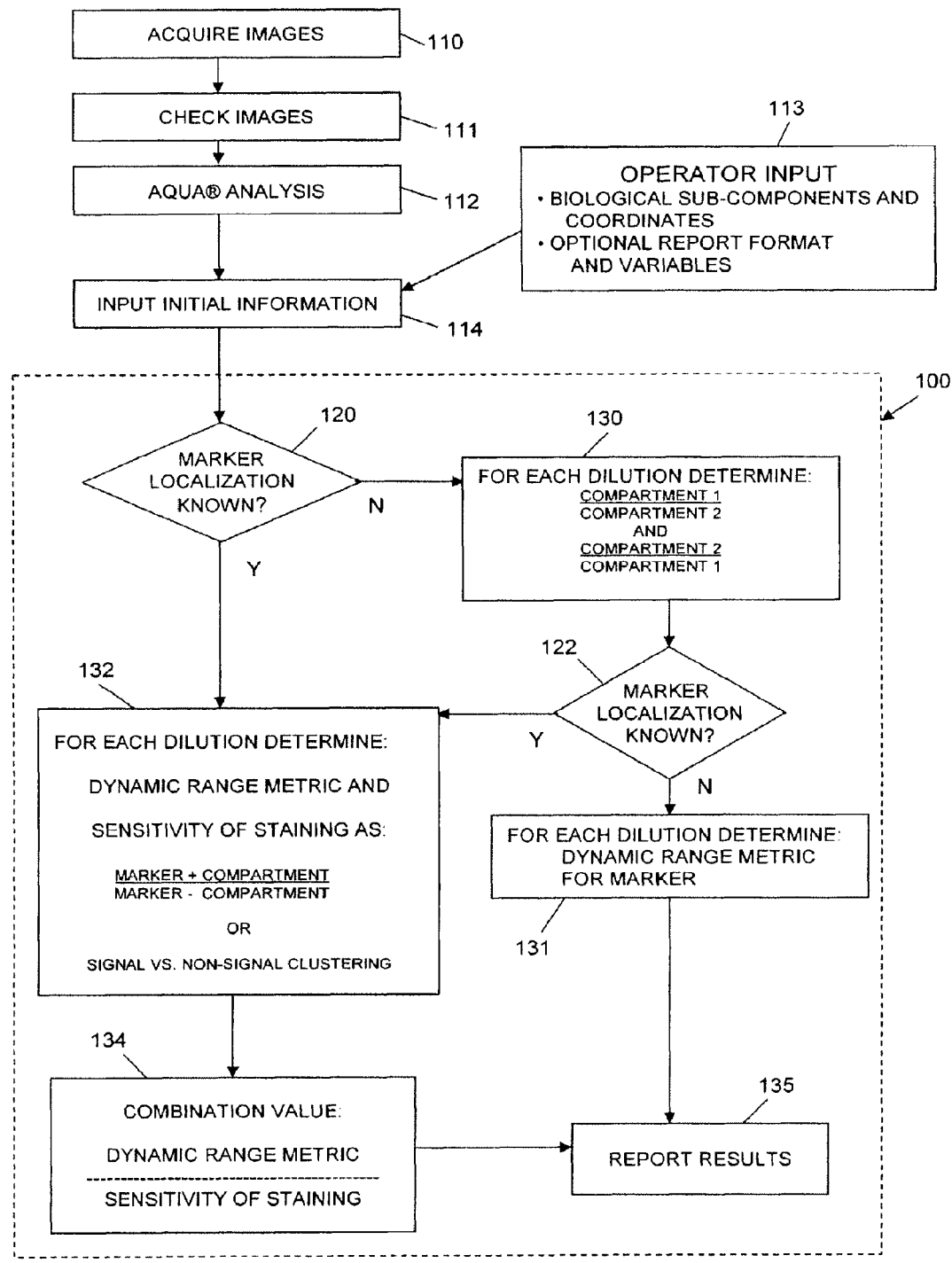
FIG. 1 is a flow diagram of a process for determining an optimal dilution of a reagent according to an embodiment of the present invention.

As is known in the art, reagents are designed to detect particular biological sub-components, for example a protein in a biological specimen. Typically, a reagent is detected by an secondary reagent and/or a detection reagent. By way of an example, a reagent may be detected by a secondary reagent comprising a fluorescent dye or an enzyme. As such, the images acquired of the stained samples consist of pixels, each pixel having a power or intensity level normalized for time of exposure. Optimally, the power or intensity level correlates with the concentration of the biological sub-components of the specimen as detected by the detection reagents. A preferred reagent for detecting a protein of interest in a sample is an antibody capable of binding to that protein, that in the context of the assay is known as a primary antibody. The secondary reagent can also be an antibody, known as a secondary antibody that is specific for the species of the primary antibody. The secondary antibody typically has a detectable label. Antibodies within the scope of the present invention include, e.g., but are not limited to, monoclonal, polyclonal, chimeric, humanized, diabody, and human monoclonal and human polyclonal antibodies which specifically bind the target polypeptide, a homolog, derivative or a fragment thereof. The antibodies useful as binding agents of the present invention include, e.g., but are not limited to, IgG (including IgG1, IgG2, IgG3, and IgG4), IgA (including IgA1 and IgA2), IgD, IgE, or IgM, and IgY.

In general, an optimal concentration for use of a primary antibody in an immunoassay is determined in an initial experiment that evaluates a plurality of antibody titrations on a biological specimen. For example, a dilution series of an antibody such as different dilutions having ratios of 1:10, 1:25, 1:100, 1:500 is tested, each dilution on a separate sample of the same biological specimen. For example the biological specimen may be a tissue sample and each dilution is tested on a histological tissue section of the specimen, ideally serial sections of the specimen. In a preferred embodiment, the each dilution of reagent is tested on multiple biological specimens representative of those intended for the analytical assay. For any particular dilution, sections so prepared for the different biological specimens can be referred to as a dilution set—different tissue samples prepared with a common dilution. In a preferred embodiment the biological specimens may be a tissue microarray (TMA) comprised of tissue samples taken (e.g., cored) from numerous different histological tissue blocks. A separate TMA section on a slide and stained with one of the dilution series of the primary antibody utilizing common IHC techniques. The resulting stained specimens are each imaged using a system for viewing the detectable signal and acquiring an image, such as a digital image of the staining. The images thus obtained are then used by the method of the invention for quantitatively determining the optimal concentration of the reagent for quantitative immunoassay studies.

An overview of a system and method of the invention for determining an optimal dilution of a reagent is shown in the flow diagram in FIG. 1. In one embodiment of the present invention, a set of images of stained samples are acquired as shown in step 110. Each of the images portrays a respective sample stained with a particular concentration of a reagent to be optimized.

Following the acquisition of a set of images, those images are preferably quality checked in step 111. The quality of an image being suitable for quantitative immunoassay can be determined manually or automatically as described in U.S. patent application Ser. No. 12/186,294 entitled "Methods and System for Validating Sample Images for Quantitative Immunoassays" filed on Aug. 5, 2008, which application claims the benefit of U.S. Provisional Application No. 60/954,303, filed on Aug. 6, 2007, each incorporated herein by reference in their entirety. Following the quality check of step 111, the images are subjected to a quantification analysis such as an AQUA analysis as shown in step 112 (AQUA is a registered trademark of HistoRx Corp. of New Haven, Conn.). AQUA analysis is further described in U.S. Pat. No. 7,219,016, the entire contents of which are incorporated herein by reference, and in Camp et al. 2002 Nature Medicine 8(11)1323-1327. The results of a quantification analysis is the production of a plurality of staining intensity values corresponding to the plurality of biological specimens assay with each of the plurality of dilution sets. Each of these dilution sets are inputted into the optimization analysis resulting in an identification of one of the dilution sets representing an optimal dilution of a reagent for use in a quantitative immunoassay 100 by way of an initial input step as shown by 114.

Additionally, an operator may input initial information into the analysis 100 through step 113. For example, in step 113 an operator may enter information indicating what reagent dilution level of the reagent was used for each particular image of stained sample. In another embodiment, more than one dilution level of the reagent may be utilized, each for a separate stained sample. In such an embodiment, an operator in step 113 may enter information indicating what reagent dilution level was used for a particular location on an image of a particular stained sample. An operator may also enter information corresponding to the style of the report following the optimization analysis the operator desires as well as a set of pre-determined variables useful in the analysis, in step 113. Further, in step 113 an operator may also enter information indicating where particular stain specific compartments are located in a stained image if those compartments are known. A stain specific compartment contains biological sub-components that the reagent is designed to detect, such as nuclei, cytoplasm, or cellular walls. Correspondingly, an operator in step 113 may enter information indicating where particular non-stain specific compartments are located in a stained image if those compartments are known. A non-stain specific compartment does not contain biological sub-components that the reagent is designed to detect. By way of example, an operator may indicate where certain tissue sub-groups (such as breast or colon cancer samples) are located in a TMA on a slide to be evaluated, and their coordinates. Furthermore, an operator may indicate that the reagent is known to specifically stain a stain specific compartment (such as tumor tissue as opposed to stroma), or a stain specific sub-cellular compartment (such as cell nuclei). Therefore, the expectation is that if such information is available the reagent's marker will be expressed in the stain specific compartments while not being expressed in the non-stain specific compartments, this differential being utilized in particular aspects of the invention. In yet another embodiment of the present invention, knowledge of the stain specific and non-stain specific compartments is known following the quantification analysis in step 112 or through step 130.

For each dilution set, the existence of such reagent or marker localization information is determined in a decision step 120. If the marker localization information is not available for a particular dilution set, the optimization analysis 100 attempts to discern such information in step 130, otherwise step 132 (calculation of a specificity of staining which requires knowledge of marker localization and calculation of a dynamic range metric) is performed. Ratios for each of the different compartments are formulated, the largest ratio indicative of marker compartment localization (step 130). In more detail, the marker localization information is determined by comparing staining intensity values of two compartments of the biological specimen(s) of a particular dilution set. By way of example, there may be a first compartment 1 and a second compartment 2 as indicated in step 130. An average staining sensitivity value is calculated for compartment 1 from the set of immunoassay staining sensitivity values determined to be associated with compartment 1. Also, an average staining sensitivity value is calculated for compartment 2 from the set of immunoassay staining sensitivity values determined to be associated with compartment 2. Once these two numbers have been calculated, a ratio of compartment 1 divided by compartment 2 and a ratio of compartment 2 divided by compartment 1 are each calculated. If either of these ratios are greater than or equal to an upper threshold quantity, e.g., 1.5, or less than or equal to a lower-threshold quantity, e.g., 0.666, then it indicates that the marker specific reagent localizes to the compartment with the numerically largest average staining intensity value.

In some embodiments of the present invention, the optimization analysis performs multiple comparisons to attempt to identify multiple stain specific and non-stain specific compartments. If after step 130 the optimization analysis is able to determine at step 122 the marker localization information step 132 is performed, otherwise step 131 is performed. In particular, step 132 performs the calculation of a dynamic range metric as well as a sensitivity of staining, whereas step 131 performs the calculation of a dynamic range metric. Following the completion of either steps 131 or 132, the results of the optimization analysis 100 are reported in step 135.

In step 132, for each dilution set of the multiple dilution sets, a dynamic range metric and a sensitivity of staining are each calculated. Each of these quantities are discussed in more detail below. Following the calculation of the dynamic range metric and sensitivity of staining for each of the dilution sets, the dynamic range metric and sensitivity of staining can be combined with one another to generate a combination value for each dilution set. The resulting combination values are used to select the dilution set with the most numerically optimal combination value. Associated with the selected dilution set is a dilution value representative of an optimal dilution of a reagent. The results of the selection are reported in step 135.

Generally, a large dynamic range is preferred, or optimal. Depending upon the metric used to define the dynamic range, the optimal dynamic range metric may be a numerically large number or a small number. Similarly, a greater or maximal sensitivity of staining is preferred, or optimal. Depending upon the metric used to define sensitivity, an optimal sensitivity metric may be a numerically large number or a small number. A combination value can be formed as a combination of the dynamic range metric and sensitivity metric. An overall optimal value can be determined by such a combination value indicating the greatest dynamic range balanced with the greatest sensitivity.

Figure 6:
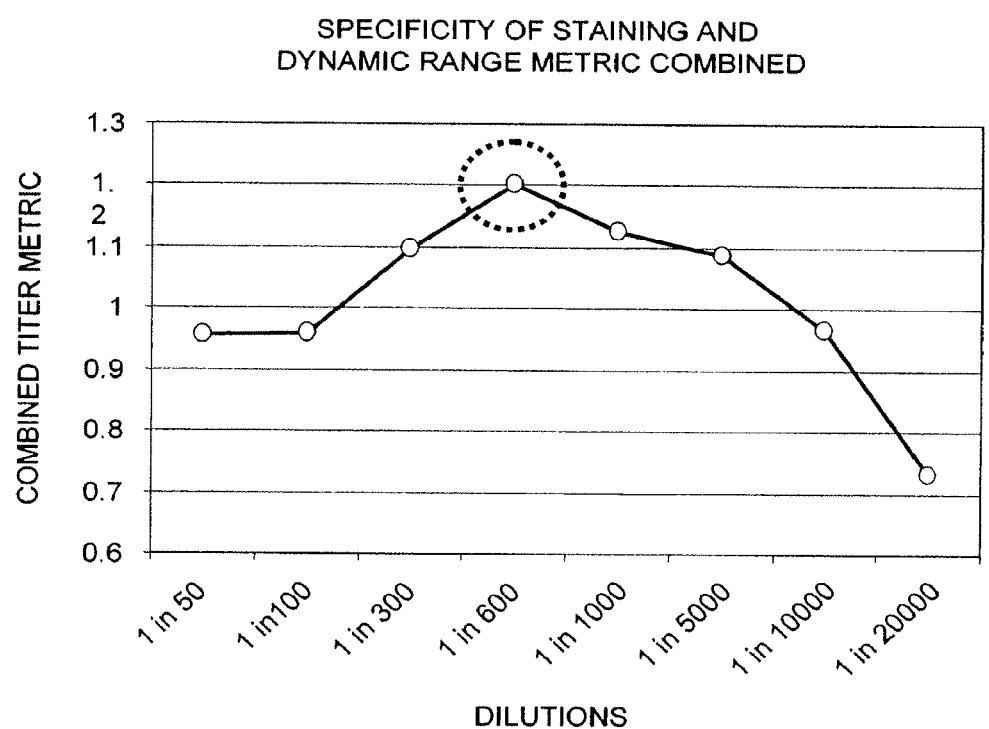
FIG. 6 is a graph illustrating determination of an optimal dilution of a reagent based on a combination of specificity of staining and a dynamic range metric according to an embodiment of the present invention.

FIG. 6 graphically illustrates a combination of a specificity of staining value and a sensitivity of staining value, such as a Dynamic Range Metric, to provide a combined metric (e.g., a sensitivity-specificity metric) for each of several different exemplary dilutions of a reagent identified along the horizontal axis. In this example, the two features in combination, the sensitivity-specificity metric resulted in the 1:600 dilution of a reagent having the greatest numeric value resulting in that dilution being selected as the most optimal.

Figure 7A:
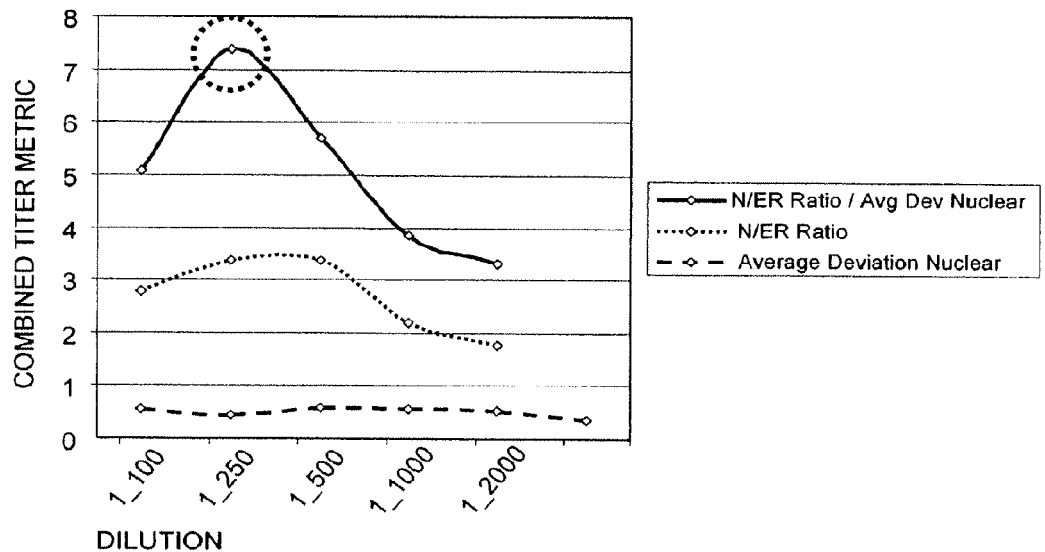
FIG. 7A is a graph illustrating determination of an optimal dilution of a reagent based on a combination of specificity of staining and a dynamic range metric according to an embodiment of the present invention.
Figure 7B:
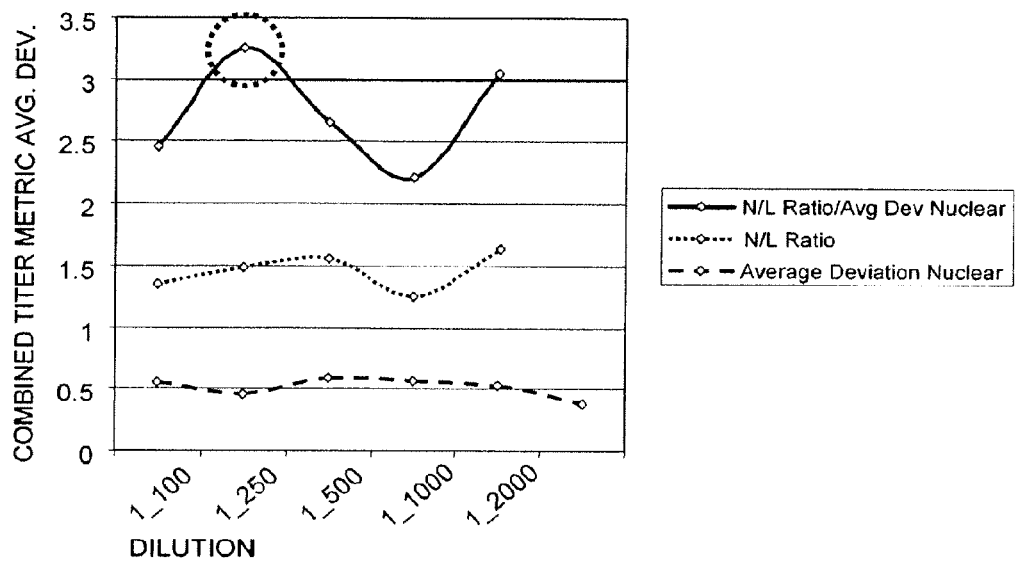
FIG. 7B is a graph illustrating determination of an optimal dilution of a reagent based on a combination of specificity of staining and a dynamic range metric according to another embodiment of the present invention.

FIG. 7A and FIG. 7B also illustrate the combination of a specificity of staining value, signal to noise metric (N/ER ratio) and a Dynamic Range Metric (AAD) to provide a sensitivity-specificity metric (N/ER Ratio/Avg Dev Nuclear [which is AAD]) for each of several different exemplary dilutions of a reagent. FIG. 7A was generated from one set of samples, while FIG. 7B was generated from another set of samples. FIG. 7A graphically illustrates both the specificity of staining value (N/ER Ratio) as well as the dynamic range metric (Average Deviation Number). In FIG. 7A, the dynamic range metric was fairly consistent, i.e., flat, but the specificity of staining value indicated that either of the 1:250 or 1:500 dilution of a reagent could be optimal. However, when the two features are combined (N/ER/Avg Dev Nuclear) as shown in the top curve of FIG. 7A, the 1:250 dilution of a reagent had the greatest numeric value resulting in that dilution being selected as the optimal dilution.

In FIG. 7B, the dynamic range metric indicated that a dilution of 1:250 may be optimal, while the specificity of staining indicated that the dilution of 1:2000 may be optimal. However, when the two features are combined as shown in FIG. 7B, the 1:250 once again had the greatest numeric value resulting in that dilution being selected as the most optimal. FIG. 7A and FIG. 7B all together illustrate how the two features can be utilized effectively in combination to balance the specificity of staining with the dynamic range metric to ultimately select an optimal dilution of a reagent.

Referring now again to FIG. 1 in step 131, for each dilution set of the multiple dilution sets the optimization analysis calculates a dynamic range metric for each one of the plurality of dilution sets. Following the calculation of the dynamic range metrics for each one of the multiple dilution sets, a dilution set is selected with the most numerically optimal dynamic range metric. Associated with the selected dilution set is a dilution value which is representative of an optimal dilution of the reagent. A dynamic range metric is optimal as a numerically large number. The results of selecting the most numerically optimal dilution set along with the optimal dilution value of the reagent are reported in step 135.

Figure 2:
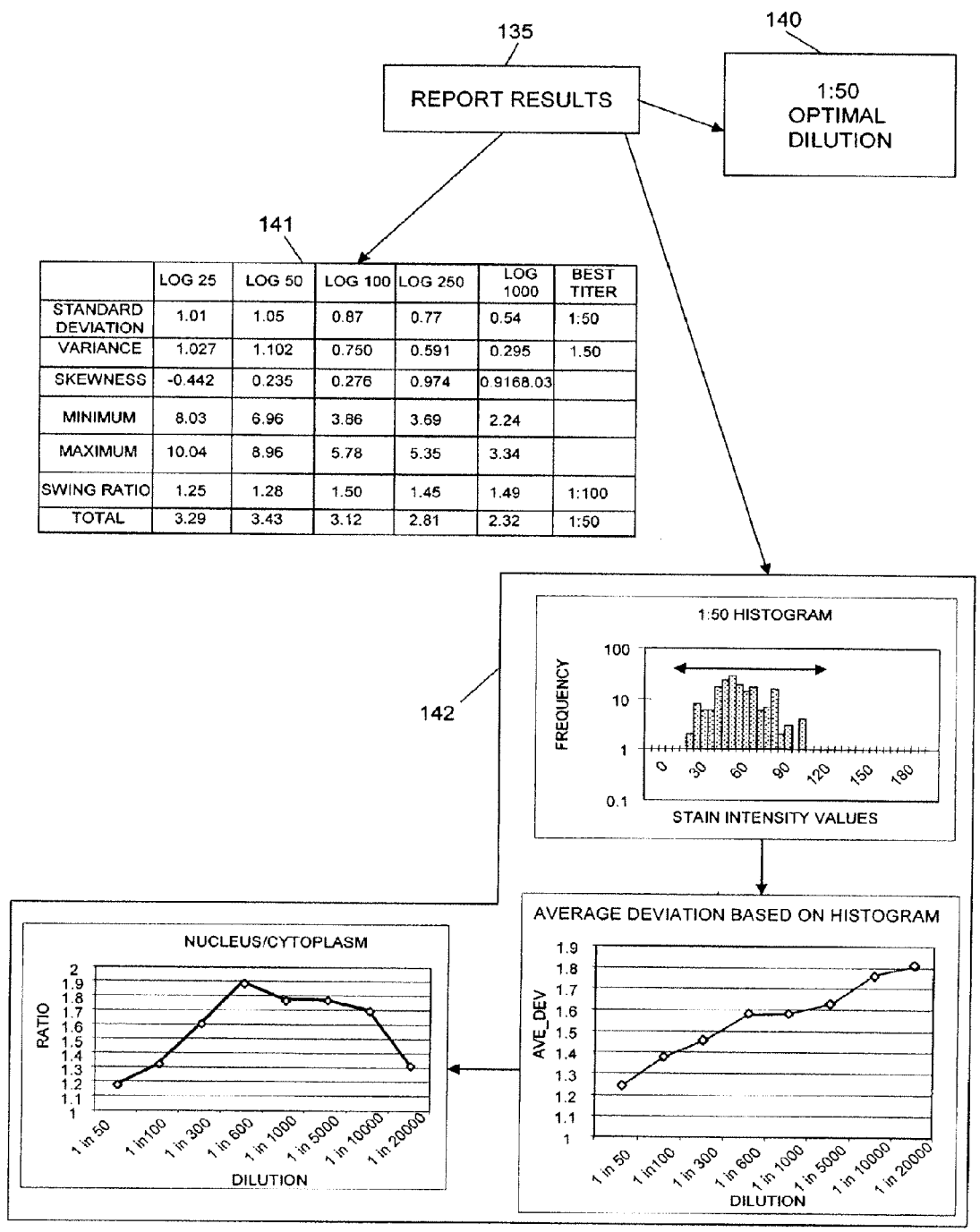
FIG. 2 is a flow diagram illustrating how results of the optimization analysis are presented in an exemplary embodiment of the present invention.

Referring now to FIG. 1 in combination with FIG. 2, the flow diagram of FIG. 2 illustrates how the results of the optimization analysis 100 can be reported 135. A report may include: a dynamic range metric, such as a copy of the histogram 142a or AAD graph 142b (as illustrated); a signal to noise metric, such as a ratio 142c (as illustrated) or a cluster analysis; and 3) the sensitivity-specificity metric obtainable by combining both (e.g., as shown in FIG. 6—can use the AAD graph 142b, the nucleus cytoplasm ratio graph 142c and the graph illustrated in FIG. 6, combined graphically as a report output). In particular, the dilution level of the selected optimal dilution can be reported at step 140. In one embodiment of the present invention data from the analysis supporting the selection of a particular optimal dilution may also be reported at step 141. In yet a further embodiment, sets of graphs and histograms can be reported at step 142 to support the selection of a particular optimal dilution. Additionally, as previously discussed, a user may indicate at step 113 (FIG. 1) how that user desires a report from step 135 to be presented.

Figure 3A:
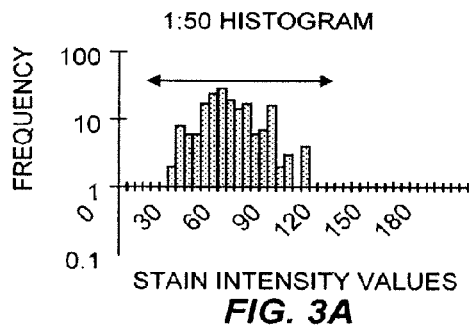
FIG. 3A through FIG. 3H together illustrate a set of exemplary histograms for a variety of different reagent dilution levels plotting frequency of an immunoassay staining intensity values.
Figure 3B:
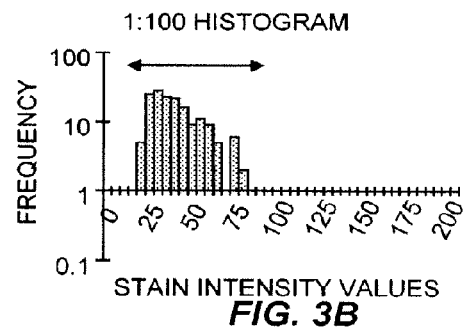
Figure 3C:
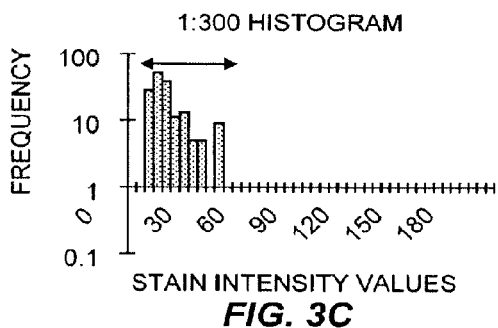
Figure 3D:
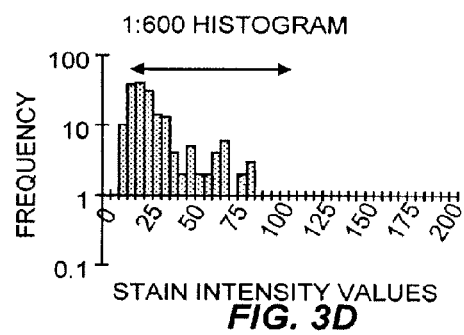
Figure 3E:
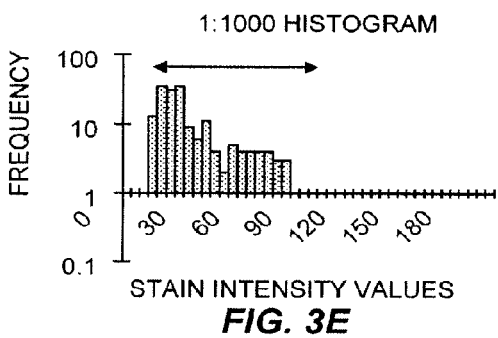
Figure 3F:
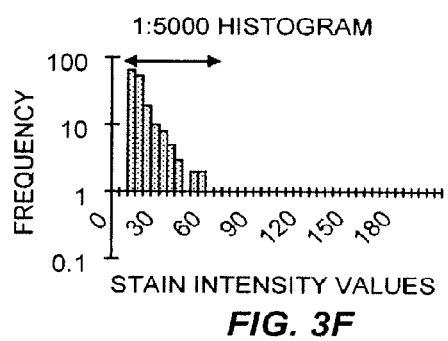
Figure 3G:
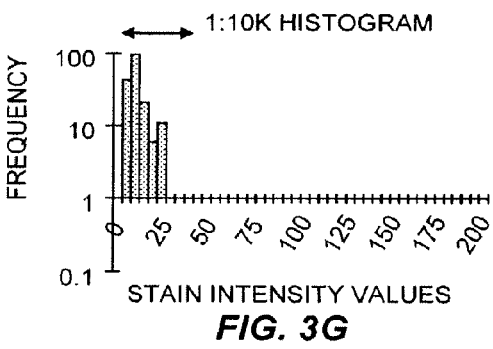
Figure 3H:
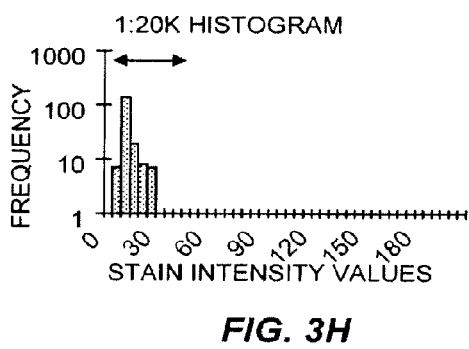
Figure 4:
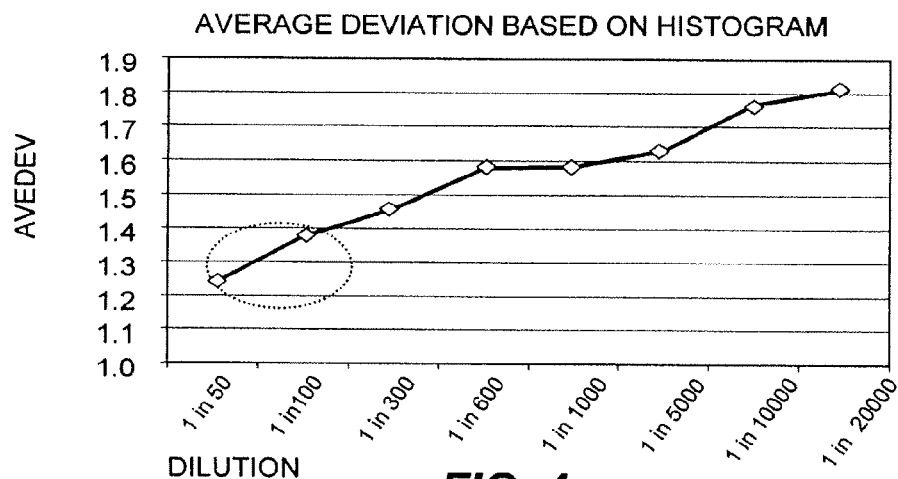
FIG. 4 is a graph illustrating a relationship between an average absolute deviation obtained from histograms of collected immunoassay staining intensity values for a variety of different reagent dilution levels and the respective dilution levels.

Referring now to the calculation of a dynamic range metric in more detail, the dynamic range metric can be used as a proxy of the spread of a particular diluted reagent's detection pattern. For instance, FIG. 3A is a histogram illustrating a frequency of particular immunoassay staining intensity values for a sample, in this case a collection of samples in a TMA format treated with a 1:50 dilution. As further illustrated by the histogram of FIG. 3A, the 1:50 dilution has a wide spread of stain intensity values (i.e., a spread of between about 50 and about 135), wherein the spread represents the ability of the assay to utilize the reagent at that concentration to accurately detect a marker across this range of expression in tissue sections. Note the impact of antibody concentration on the dynamic range of the provided data. For instance in comparison with the histogram of FIG. 3G, illustrating the frequency of particular immunoassay staining intensity values for a sample (the TMA) treated with a 1:10,000 dilution, the 1:10,000 dilution has a narrower (i.e., a spread of between about 5 and about 30) a spread of and therefore less than optimal dynamic range spread. Consequently, the 1:10,000 dilution of the reagent likely caused fairly severe under-detection as previously discussed in this detailed description. Indeed, as one progresses along through the varying dilutions of FIG. 3A (1:50 dilution), FIG. 3B (1:100 dilution), FIG. 3C (1:300 dilution), FIG. 3D (1:600 dilution), FIG. 3E (1:1000 dilution), FIG. 3F (1:5000 dilution), FIG. 3G (1:10,000 dilution), and FIG. 3H (1:20,000 dilution), the dynamic range of the data tends to decrease substantially. This feature of the dilution values is captured in the graph FIG. 4, showing how the average deviation increases substantially as the reagent becomes more diluted. In one embodiment of the present invention, the dynamic range metric is an average absolute deviation (AAD), and an optimal dynamic range metric is a numerically small value which represents the best spread of data. In another embodiment of the present invention, the dynamic range metric is a weighted combination of a standard deviation, a variance, and a swing ratio, and an optimal dynamic range metric is a numerically large value which represents the best spread of data.

Referring now to the calculation of a dynamic range metric in more detail, the dynamic range metric can be used as a proxy of the spread of a particular diluted reagent's detection pattern. For instance, FIG. 3A is a histogram illustrating a frequency of particular immunoassay staining intensity values for a sample treated with a 1:50 dilution. As further illustrated by the histogram of FIG. 3A, the 1:50 dilution has a wide spread of stain intensity values, wherein the spread represents the ability of the reagent to accurately express itself in areas where there are instances of the biological sub-components that the reagent is designed to detect. Note the impact of antibody concentration on the dynamic range of the provided data. For instance in comparison with the histogram of FIG. 3G, illustrating the frequency of particular immunoassay staining intensity values for a sample treated with a 1:10,000 dilution, the 1:10,000 dilution has a narrower and therefore less than optimal spread. Consequently, the 1:10,000 dilution of the reagent likely caused fairly severe under-detection as previously discussed in this detailed description. Indeed, as one progresses along through the varying dilutions of FIG. 3A (1:50 dilution), FIG. 3B (1:100 dilution), FIG. 3C (1:300 dilution), FIG. 3D (1:600 dilution), FIG. 3E (1:1000 dilution), FIG. 3F (1:5000 dilution), FIG. 3G (1:10,000 dilution), and FIG. 3H (1:20,000 dilution), the dynamic range of the data tends to decrease substantially. This feature of the dilution values is captured in the graph FIG. 4, showing how the average deviation increases substantially as the reagent becomes more diluted. In one embodiment of the present invention, the dynamic range metric is an average absolute deviation. In another embodiment of the present invention, the dynamic range metric is a weighted combination of a standard deviation, a variance, and a swing ratio Referring to embodiments of the present invention in which the dynamic range metric is an average absolute deviation, the calculation initially involves the calculation of a mean $\overline{Y}$ of all of the plurality of immunoassay staining intensity values of a dilution set (i.e., for the different tissue samples prepared with a common dilution). Once the mean has been calculated, each immunoassay staining intensity value $Y_i$ from the plurality is subtracted from the mean and an absolute value is taken resulting in an absolute deviation from the mean. All of the absolute deviations from the mean for each plurality of immunoassay staining intensity values are summed together and divided by the total number N of the plurality of immunoassay staining intensity values. The resulting value is an average absolute deviation ADD. While standard deviation calculations could also be used, the average absolute deviation method does not square the distance between the mean and therefore is less affected by extreme values (i.e., the tails of the data distribution). In this particular embodiment, the most optimal dynamic metric range is the numerically greatest number. In traditional mathematical formula terms, the average absolute deviation is calculated as:

$$ADD = \sum_{i=1}^{n} (|Y_i - \overline{Y}|)/N$$

Referring now to alternative embodiments of the present invention, the data can be log transformed and the Dynamic Range Metric can be formulated as a weighted combination of a standard deviation, a variance, and a swing ratio. A standard deviation is a measure of the spread of a multi-set of values, such as the arrangement of staining sensitivity values. A standard deviation can be calculated by mathematically comparing the value of a number with the expected value of that number. The values compared can be those of the arrangement of immunoassay staining intensity values, such that the expected value is the mean of the arrangement of immunoassay staining intensity values. The calculation of a standard deviation for an arrangement of immunoassay staining intensity values begins by calculating the mean of the arrangement of staining intensity values. For each one of the plurality of staining intensity values, the mean can be subtracted from the value and the square of the result taken to produce a deviation value. All of the deviation values for each of the different arrangements of immunoassay staining intensity values can be summed together and divided by the total number of the different arrangements of staining intensity values and a square root of the result can be taken to produce a standard deviation. In traditional mathematical formulaic terms, a standard deviation is calculated as follows:

$$\sigma = \sqrt{\frac{1}{N}\sum_{i=1}^{n}(x_i - \overline{x})^2}$$

Where σ is the standard deviation, $x_i$ is each individual one of the arrangements of immunoassay staining intensity values, x "bar" is the mean of the arrangements of immunoassay staining intensity values, N is the number of different arrangements of immunoassay staining intensity values and i is an integer varying between 1 and n.

The variance of a multi-set, such as the arrangement of immunoassay staining intensity values, is a non-negative number which provides an indication as to how widely spread the values of a multi-set are likely to be. The larger a variance, the more scattered the members of a multi-set are on average. The variance is calculated as the square of the standard deviation as discussed above. Therefore, the calculation of the variance for a plurality of immunoassay staining intensity values begins by calculating the mean of the plurality of staining intensity values. For each one of the plurality of staining intensity values, the mean is subtracted from the value and the square of the result is taken to produce deviation value. All of the deviation values for each of the different arrangements of immunoassay staining intensity values are summed together and divided by the total number of different arrangements of staining sensitivity values resulting in the variance. In traditional mathematical formula terms a variance is calculated as follows:

$$\sigma^2 = \frac{1}{N} \sum_{i=1}^{n} (x_i - \bar{x})^2$$

for which $\sigma^2$ is the variance, $x_i$ is each individual one of the plurality of immunoassay staining intensity values, x "bar" is the mean of the plurality of immunoassay staining intensity values, N is the number of plurality of immunoassay staining intensity values, and i is an integer varying between 1 and n.

The swing ratio of plurality of immunoassay staining intensity values is determined as an average of a selected number of the highest-valued immunoassay staining intensity values divided by an average of a selected number of the lowest-valued immunoassay staining intensity values. In some embodiments of the present invention, a number of the highest and lowest numbers are utilized to calculate the swing ratio. In some embodiments of the present invention, the arrangement of immunoassay staining intensity values are logarithmically transformed prior to further manipulation as in calculating the swing ratio. In some embodiments of the present invention, the logarithm utilized is to the second base.

As mentioned previously, the embodiment currently being discussed is such that the dynamic range metric is a weighted combination of a standard deviation, a variance, and a swing ratio. In one embodiment of the present invention, each of the factors of a standard deviation, a variance, and a swing ratio are each weighted by multiplying each of the factors by the integer one and all three weighted results summed together to produce the dynamic range metric. In some embodiments of the present invention, each of the factors of a standard deviation, a variance, and a swing ratio are weighted by multiplying one or more of the factors by a respective weighting value and summing all three weighted results together to produce a dynamic range metric. In still other embodiments of the present invention, each of the factors of a standard deviation, a variance, and a swing ratio are weighted by multiplying one or more of the factors by a respective weighting value and multiplying all three results together to produce a dynamic range metric.

Figure 5A:
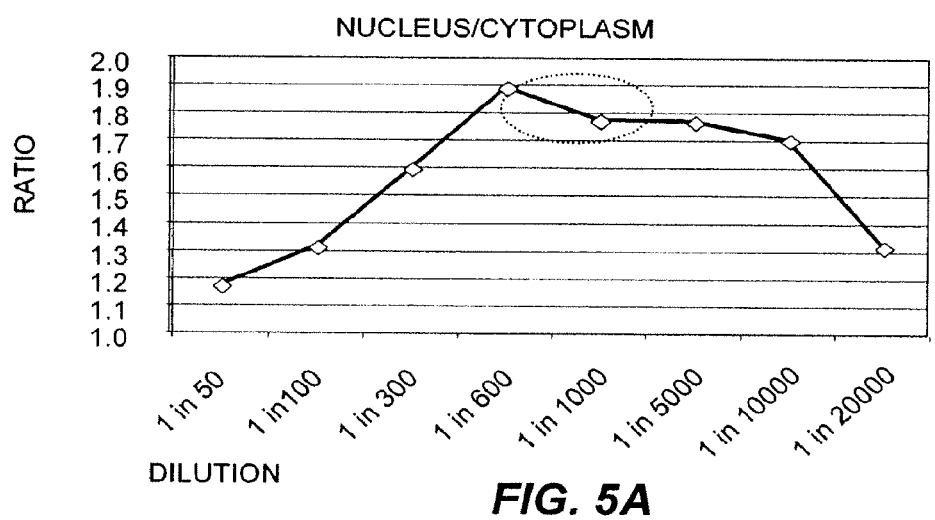
FIG. 5A and FIG. 5B are a set of graphs illustrating a relationship between a dilution level and a sensitivity of staining determined according to an embodiment of the present invention.
Figure 5B:
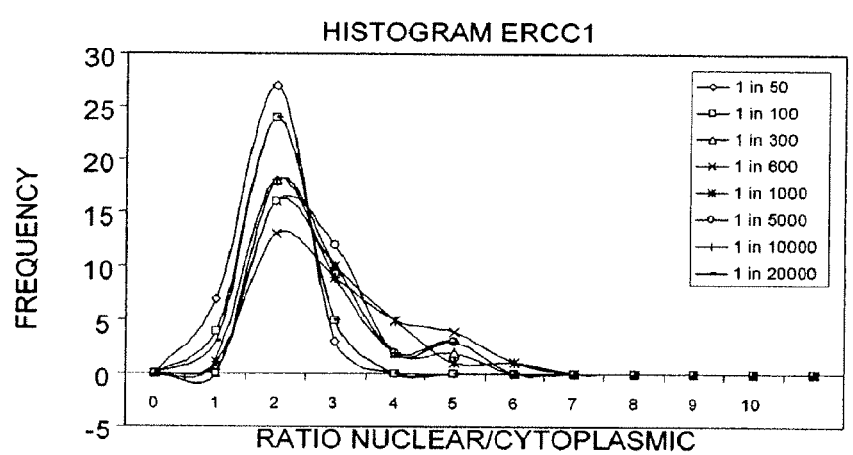

The specificity of the immunoassay staining intensity associated with a stain specific compartment in a dilution set is evaluated in one embodiment by the calculation of a specificity of staining which involves comparing a first set of immunoassay staining intensity values measured for a stain specific compartment to a second set of immunoassay staining intensity values associated with a non-stain specific compartment in a dilution set. The purpose of such a comparison is to determine the optimal reagent titer that maximizes specific signal while minimizing noise. In one embodiment the specificity of staining is computed by summing each of a set of immunoassay staining intensity values associated with a stain-specific compartment and then computing a stain specific average for the stain-specific compartment, and also summing each of a set of immunoassay staining intensity values associated with a non-stain specific compartment and then computing a non-stain-specific average. Following the calculation of these two averages, the stain specific average can be divided by the non-stain specific average to produce the specificity of staining, or a Signal to Noise Metric. In such an embodiment, a numerically large sensitivity of staining value is optimal. In another embodiment the non-stain specific average is divided by the stain specific average to produce the sensitivity of staining. In such an embodiment, a numerically small sensitivity of staining value is optimal. FIG. 5A and FIG. 5B illustrate the specificity of staining feature. In FIG. 5A illustrating an exemplary specificity of staining, the stain specific biological sub-component was a nucleus whereas the non-stain specific biological sub-component was the cytoplasm of a cells in the tissue sample. The ratio shown in FIG. 5A is the stain specific average divided by the non-stain specific average, therefore an optimal value is a numerically large value. As illustrated by FIG. 5A then, the 1:600 dilution demonstrated the most specificity. FIG. 5B provides more detail by illustrating a frequency distribution illustrating the specificity of staining values obtained from multiple treated samples and for multiple dilutions. The ratio in FIG. 5B is the stain specific average divided by the non-stain specific average, therefore an optimal value is a numerically large value. The dilution of the reagent showing the greatest shift to the right of the graph has the best sensitivity of staining In FIG. 5B, a dilution of 1:600 is shown as having the best sensitivity of staining.

Referring again to FIG. 1, in some instances the quality of the data to be input into the optimization analysis resulting in an optimal dilution of a reagent for use in a quantitative immunoassay 100 can be checked prior to, at, or after step 114 (FIG. 1). In step 114, in one embodiment the plurality of staining sensitivity values for each dilution set are initially logarithmically transformed. In one embodiment of the present invention a base 2 logarithm is used. Following the transformation, each of the arrangements of immunoassay staining intensity values are subjected to a regression analysis. Following the regression analysis the results are compared against a regression criteria indicative of an established quality. If the results are such that they do not meet an established quality criterion the dilution set can be removed from the optimization analysis at step 114. In one embodiment of the present invention the regression analysis performed is parametric, such as a Pearson's R regression analysis. In still another embodiment of the present invention, the regression analysis performed is non-parametric, such as a Spearman's Rho regression analysis. FIG. 10 illustrates the utilization of a parametric Pearson regression to examine data in one embodiment of the present invention. In the table of exemplary values illustrated in FIG. 10, all of the data correlated well and so all the data was used for the analysis. The table of exemplary values illustrated in FIG. 12 also demonstrates the utilization of a parametric Pearson regression to examine data. The data in FIG. 12 all correlated well so all the data was also used for the analysis. The table of exemplary values illustrated in FIG. 11 demonstrates the utilization of a non-parametric Spearman regression to examine data in one embodiment of the present invention. In FIG. 11, all of the data correlated well and so all the data was used for the analysis. FIG. 13 also illustrates the utilization of a non-parametric Spearman regression to examine data. The data in FIG. 13 all correlated well so all the data was used for the analysis. Had one or more of the dilution sets not correlated well, such poor correlation would be indicative of a lack of quality in the associated data set. In some embodiments, dilution sets having poor correlation are excluded.

In addition to the application of a logarithmic transform and regression test, step 114 a quality analysis can also be achieved by examining other parameters, such as the skewness of a particular set of immunoassay staining intensity values. The skewness of a particular set of immunoassay staining intensity values aids in determining whether the values assume a normal or near-normal distribution. That is, skewness is a measure of the asymmetry of a probability distribution of a collection of random values, such as those in the plurality of immunoassay staining intensity values associated with each dilution set. A skewness value of '0' indicates a completely normal distribution. A negative value indicates a left-sided distribution tail with most values having a higher value. A positive value indicates a right-side distribution tail with most values having a lower value. It is generally understood that skewness values that fall outside the range of about −2 to 2 are significantly deviating from normal. In another embodiment, a narrower skewness, for example in the range of about −1.5 to 1.5 can be considered to comprise an unacceptable range. Embodiments typically include ranges of between about −2 and −1.5 and between about 2 and 1.5 as an acceptable range. If a skewness falls outside of the acceptable range, the dilution set can be discarded or at least not analyzed further by the optimization analysis 100.

The skewness value $g_1$ can be calculated at step 114 (FIG. 1) by first calculating the mean value of the arrangement of sensitivity staining values. Following the calculation of the mean, for each of the different arrangements of immunoassay staining intensity values the mean is subtracted from the immunoassay staining intensity value resulting in a difference. The difference is then taken to the $3^{rd}$ power and each of the results of this calculation for each immunoassay staining intensity value are added together in to a top sum. The top sum is then multiplied by the square root of the total number of values in the arrangement of staining sensitivity values. Taking again the differences previously calculated, those differences are squared and each of the results are added together to produce yet another result which is taken to the 1.5 power which results in a bottom sum. The skewness value $g_1$ can be calculated for each dilution set as the top sum divided by the bottom sum. In traditional mathematical formula terms a skewness is calculated as follows:

$$g_1 = \frac{\sqrt{n} \sum_{i=1}^{n} (x_i - \bar{x})^3}{\left( \sum_{i=1}^{n} (x_i - \bar{x})^2 \right)^{3/2}}$$

for which $g_1$ is the skewness value, $x_i$ is each individual one of the plurality of immunoassay staining intensity values, x "bar" is the mean of the plurality of immunoassay staining intensity values, n is the number of plurality of immunoassay staining intensity values and i is an integer varying from 1 to n.

Referring now to the calculation of the signal to noise metric in step 134 (FIG. 1), in some embodiments, this calculation only occurs if the optimization analysis 100 is to include this factor in its selection of the optimal dilution set. Preferably, a signal to noise metric for a dilution set is a numerically large number indicating a substantial value of signal presence with respect to noise. The signal to noise metric can be calculated by taking advantage of the dynamic range of the image pixels as represented in the arrangement of immunoassay staining intensity values. An optimal dilution set will have the greatest dynamic range of the different arrangements of immunoassay staining intensity values. An optimal dynamic range exists after two clusters have been formulated in a sub-group of immunoassay staining intensity values in the different arrangements of immunoassay staining intensity values. A first cluster represents a signal cluster indicative of the reagent's marker being the most frequently and most intensely expressed among the immunoassay staining intensity values of interest. This cluster likely represents specific staining of biological sub-components that the reagent is designed to detect (i.e., tumor-specific immunoassay staining intensity values such as those defined by an anti-cytokeratin antibody). Additionally, a second cluster represents a noise cluster indicative of the reagent's marker being not as frequently expressed nor as intense and represents instances where the reagent resulted in inaccurate identification or noise. Once these clusters have been defined, a distance between the center of the signal cluster and the center of the noise cluster is calculated for each set of clusters calculated for the different arrangements of immunoassay staining intensity values, resulting a signal to noise metric. Optimally, a dilution set's arrangement of staining intensities had the greatest average distance between clusters, signifying that a numerically large signal to noise metric is optimal.

Referring again to FIG. 1, the signal to noise metric (selectivity) that is combined with the Dynamic Range Metric (sensitivity) in the results of step 132 to create a signal mathematical relation. Following this combination, the dilution set having the optimal value of a signal mathematical relation determined as a combination of the Signal to Noise Metric and the Dynamic Range Metric (step 132) is selected, the associated dilution value determined, and the results reported at step 135. A signal mathematical relation is optimal when it is a numerically large number. As discussed previously, the dynamic range metric calculated in step 131 can be optimally either a numerically small value or numerically a large value.

In one embodiment where the marker localization is not known and can not be calculated (130), the Dynamic Range Metric may be combined with a Signal to Noise Metric calculated by the cluster analysis above resulting in a Signal Specificity Metric.

In one embodiment, where the optimal dynamic range metric calculated in step 131 is optimally a small value, the dynamic range metric from step 131 is inverted and then mathematically related to the signal to noise metric 134 to create the signal mathematical relation. In another embodiment in which the optimal dynamic range metric calculated in step 131 is optimally a large value, the dynamic range metric from step 131 is mathematically related to the signal to noise metric to create the signal mathematical relation.

Figure 8:
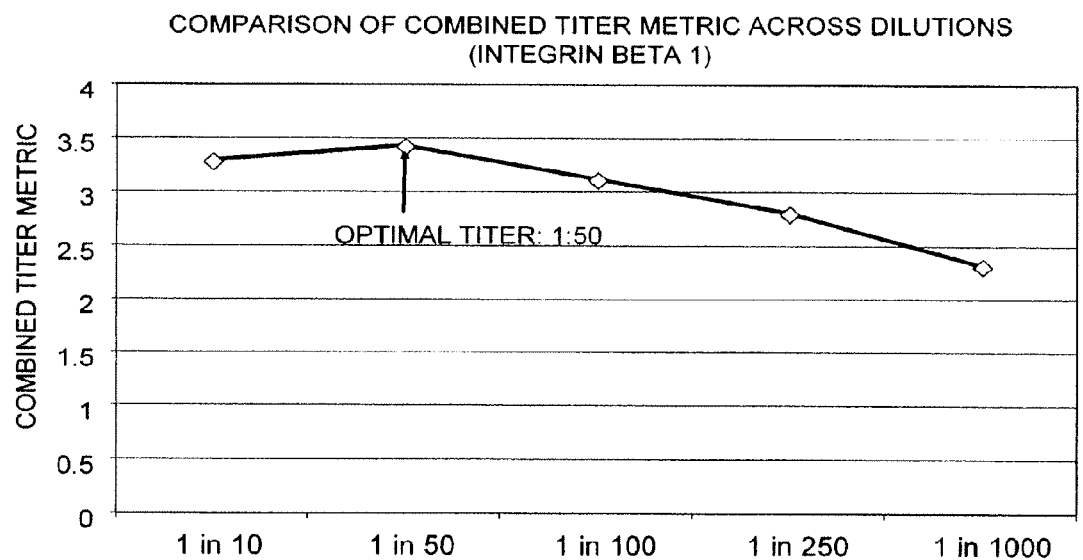
FIG. 8 is a graph illustrating determination of an optimal dilution of a reagent based on a combination of specificity of staining, a dynamic range metric, and a signal to noise metric according to an embodiment of the present invention.

In yet another embodiment in which the combination value of step 132 is optimally a numerically large value, the initial combination is mathematically related to the signal-to-noise ratio to create the signal mathematical relation. In yet another embodiment in which the combination value of step 132 is optimally a numerically small value, the combination value is inverted and then mathematically related to the signal to noise metric to create a signal mathematical relation. In some embodiments, it is possible to combine the specificity by the compartment ratio together with specificity by the signal to noise metric. FIG. 8 graphically illustrates the combination of a sensitivity of staining value (signal to noise) by cluster analysis with a dynamic metric value by SD+V+ratio analysis for different dilutions. In combining all these features, the 1:50 dilution is identified as the optimal dilution of a reagent, because it has the largest combined value.

The tables of FIG. 14 and FIG. 16 illustrate how all the numerical factors discussed as one embodiment in this detailed description can be combined to determine an optimal reagent dilution for use in a quantitative immunoassay. In particular, in FIG. 14 the factors of standard deviation, variance, and the swing ratio are combined to produce a dynamic range metric for each of the sample dilutions analyzed. Further, in FIG. 14 the skewness of the data for each of the sample dilutions was analyzed to determine if the data was viable. As illustrated in FIG. 14, the 1:50 dilution had the optimal standard deviation and variance, yet the 1:100 dilution has the optimal swing ratio. However, as illustrated by the table of FIG. 14, when the features are combined the 1:50 dilution provides the optimal dilution based on the test results. As a result, FIG. 14 illustrates the novelty of using the features in combination to determine an optimal dilution of a reagent. The table of FIG. 15 represents additional data which was used in the calculation of the factors in FIG. 14. Similarly, FIG. 16 shows the same features for a different reagent and shows that for all three of the factors of standard deviation, variance, and swing ratio the 1:250 dilution was the optimal dilution. Consequently, when all the factors were combined FIG. 16 illustrates that the 1:250 dilution was selected as the optimal dilution. The table of FIG. 17 represents additional data which was used in the calculation of the factors in FIG. 15.

Figure 9:
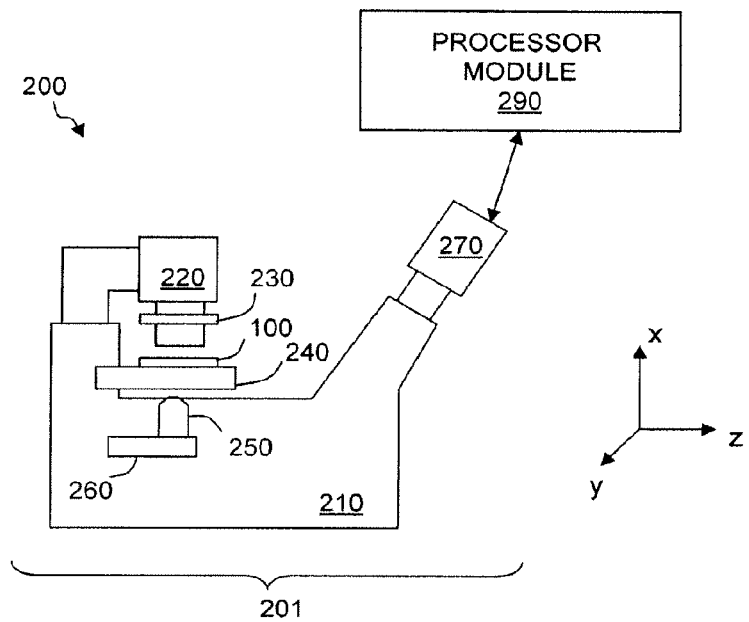
FIG. 9 is a diagram of an exemplary embodiment of a system for determining an optimal dilution of a reagent for use in a quantitative immunoassay according to an embodiment of the present invention.

Referring now to FIG. 9, which illustrates an exemplary embodiment of a system for determining an optimal dilution of a reagent for use in a quantitative immunoassay 200. As illustrated, the system 200 includes a microscope 201 configured to magnify a portion of slide-mounted tissue sample 100. The microscope typically consists of a housing light source 220, a mounting means 240, a lens 250, filter wheels 230 and 260, a mount 210, and an image sensor 270. The image sensor 270 is in optical communication with the microscope and is configured to obtain digitized images of the magnified portions of the slide-mounted tissue sample 100. In the illustrated embodiment, there is also a processor module 290 which is in communication with at least the image sensor 270. The processor module 290 is configured to (i) automatically receive a plurality of dilution sets, each dilution set having a different respective dilution value of the reagent and comprising a respective plurality of immunoassay staining intensity values, (ii) determining for each of the plurality of dilution sets a respective dynamic range metric related to the respective plurality of immunoassay staining intensity values, and (iii) identifying the dilution set having the numerically optimal dynamic range metric, the dilution value of the identified dilution set being representative of an optimal dilution level of the reagent for use in the quantitative immunoassay.

EXAMPLES

The IHC staining performed to select an optimal titer is ideally done on serial sections of tissue microarrays (TMA's) or whole tissue sections (WTS's). The staining procedure includes all antibody dilutions of interest in the same staining batch, in order to minimize inconsistencies.

The staining protocol involved deparafinization in xylene, rehydration through a series of decreasing amounts of ethanol to pure water, and antigen retrieval in Tris EDTA. After endogenous peroxidase blocking and blocking with background sniper, primary antibodies (mouse) specific for the marker of interest and cytokeratin (Rabbit, Dako) primary antibodies were applied and rinsed off after 1 hour. Dako Envision anti-mouse and Invitrogen alexa 555 GAR were then applied. After extensive washing, cy 5 tyramide was applied. The slides were then washed in TBS/Tween 20. Finally, a mounting media with DAPI was applied and the slides were dried.

Images of stained tissue sections were acquired on the PM-2000 and analyzed using AQUA® analysis resulting in an AQUA® score correlating to protein concentration.

AAD Method:
1. The AAD method was used to determine the optimal titration for use for an antibody specific for ERCC1 (mouse AB-2(8F1) LabVision). The following dilutions were tested: 1:50, 1:100, 1:300, 1:600, 1:1000, 1:5000, 1:10,000 and 1:20,000 on a lung cancer TMA of 40-50 samples. Results are shown in FIGS. 4, 5A, and 5B and indicate a titration of 1:600 is optimal.
2. The AAD method was used to determine the optimal titration for use for an antibody specific for HSP70. The following dilutions were tested: 1:100, 1:250, 1:500, 1:1000, and 1:2000 on heart tissue samples. Results are shown in FIGS. 7A and 7B and indicate a titration of 1:250 is optimal.

Combined Titer Metric Method:
1. The Combined Titer Metric Method was used to determine the optimal titration for use for an anti-integrin beta 1 antibody (LabVision mouse Mab 7F10). The following dilutions were tested: 1:25, 1:50, 1:100, 1:250, and 1:1000.

The data correlates (by Pearson correlation Table of FIG. 11 and Spearman's rho Table of FIG. 12) across all dilutions tested so all data was used for analysis.

Figure 18:
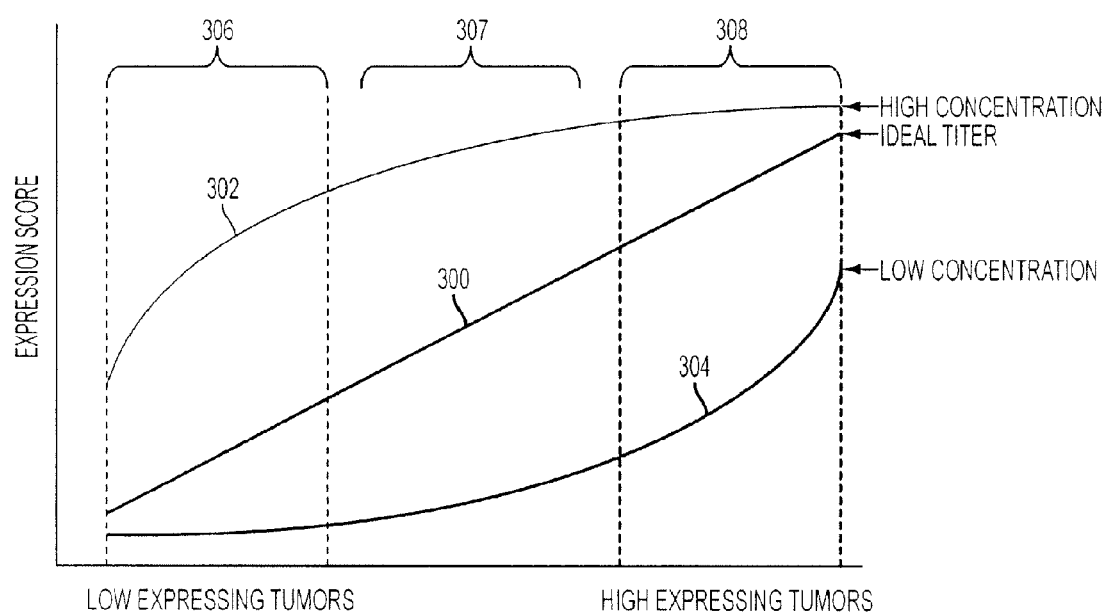
FIG. 18 is a graph illustrating an exemplary determination of an "ideal" titer.

As describes herein, optimization of antibody titer is extremely important for immunoassays, and quantitative optimization within the field of immunohistochemistry is particularly important for generating optimal quantitative results. Preferably, such optimization should involve at least two parameters:
(i) maximization of signal-to-noise for each individual sample allowing for the greatest reduction of background signal relative to specific signal; and
(ii) maximization of dynamic range across a range of samples allowing for the greatest average differentiation of "expression scores" across samples. For embodiments relying on these two parameters, the former is or can be determined using pixel-specific information inherent to digital image of IHC stained samples (for example as used in AQUA® analysis. The latter is illustrated in FIG. 18, in which samples (for example tumor specimens) can be sorted low to high along one axis (e.g., the x-axis) for "true expression" and along a different axis (e.g., the y-axis) for "virtual expression" scores. In general, FIG. 18 illustrates variation in expression scores over a range of different expressing samples (different tissue samples) arranged from low to high concentrations. An ideal or so-called perfect titer would provide a direct linear relationship 300 across an entire cohort or collection of samples. Deficient titers that may be too high or too low, will become non-linear in indicated areas of the curve 302, 304 resulting in the inability to differentiate cases based on expression score at the low end of expression (low titer) 306 or at the high end of expression (high titer) 308. Although in most all instances, a "perfect" titer 300 cannot be achieved, an optimal titer provides, on average, the most differentiation of expression scores across the range of the samples.

Because automated quantitative analyses, such as AQUA® technology provide continuous and quantitative expression values or scores based on quantitative pixel "intensities", both parameters described above can be objectively and quantitatively determined. (NOTE: traditional chromagen-based IHC methodologies only allow for subjective determination of parameter 1 without allowing any such determination of parameter 2). In at least some instances, the continuous and quantitative expression values or scores can be represented by a single numeric value for a representative image of a tissue sample. Different images of a cohort would have respective numeric values. Alternatively or in addition, more than one numeric value can be identified for each imaged tissue sample. This protocol, however, is not limited to AQUA® technology in that any technology that allows for quantification of in situ protein expression in tissue and provides quantitative pixel information could implement this protocol.

General Principles

Each parameter outlined above can be defined by at least two basic characteristics:

1. Central tendency of the middle ⅔ of population 307. Typically, for normal distributions of data whose means do not vary significantly, standard deviation represents a preferred metric. However, because most distributions of raw data (i.e., pixel intensity values or representative AQUA® scores) are non-normal, having means that can vary significantly. In such situations, standard deviations can be considered within the context of their means. A parameter referred to herein as a percent-coefficient-of-variation (% CV) is a more appropriate metric. % CV ($C_v$) is a dimensionless measure that can be determined by the following relationship:

$$c_v = \frac{\sigma}{\mu}.$$

The value σ represents a standard deviation, whereas the value μ represents a mean value. Values of percent-coefficient-of-variation being less than one (1) (% CV<1) are considered low variance; whereas, those greater than one (1) are considered high variance. The % CV can be determined for one or more of the pixel intensity values and representative AQUA® scores.

2. Dynamic range of the population extremes (high v. low). A so-called "swing ratio" can be defined as an indication of the values spanned by a variable. For example, a swing ratio can be determined a ratio between a selective set of high-values and a selective set of low values. In an exemplary swing ratio, a top 15% of values is divided by a bottom 15% of values. The values can be one or more of pixels, as in parameter 1, and AQUA® scores, as in parameter 2. In some embodiments, the values within the top and bottom selective sets are respectively combined (e.g., summed together) prior to formulation of the ratio. Alternatively or in addition, individual ratios are formed using values within the top and bottom selective sets and then combined in a representative value, such as an average ratio.

Protocol Description

Figure 19:
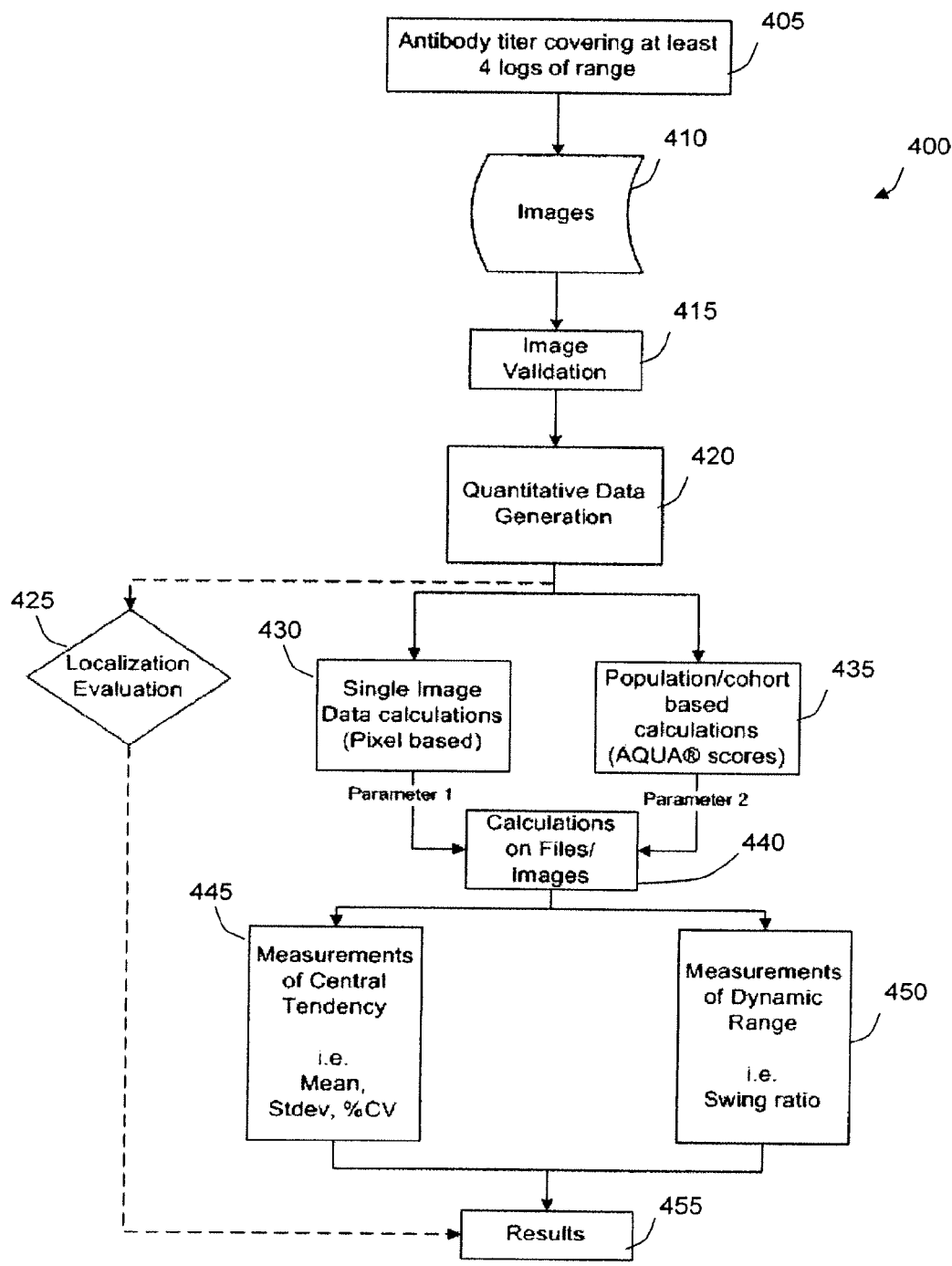
FIG. 19 is a flow chart of an exemplary quantitative tittering optimization protocol according to an embodiment of the present invention.

A flowchart of an embodiment of a quantitative titering optimization protocol 400 is presented in FIG. 19. In an initial step 405, multiple antibody titers are prepared with dilutions spanning a substantive range. In some embodiments, the antibody titers span at least four cycles of a logarithmic scale. Tissue samples are treated with the prepared titers. In some embodiments, the tissue samples are in a tissue microarray (TMA) format representing multiple tissue types. Alternatively or in addition, tissue samples can be prepared as whole tissue sections. Generally, multiple different tissue samples are treated with each of the different dilutions. Importantly, the range of titer dilutions is sufficient such that a decrease in centrally tendency and dynamic range relative to the optimal titer are observed at both ends of the titer range (see FIGS. 21A through 21D and FIGS. 22A through 22D). This so-called "bookending" or increase in magnitude of slope of each respective curve confirms that the optimal titer has been achieved.

For a quantitative analysis, such as AQUA® analysis, images of each tissue sample across each titer are obtained are acquired in step 410. One or more of these acquired images can be validated at step 415. Validation can identify stained tissue samples having undesirable artifacts, such as uneven staining, saturation, contamination, improper alignment, or folds, tears or other imperfections in the tissue sample, and proper focus of images obtained therefrom. Validated images are then entered in quantitative data generation (e.g., AQUA® score and pixel histogram generation; see below) at step 420.

Figure 20:
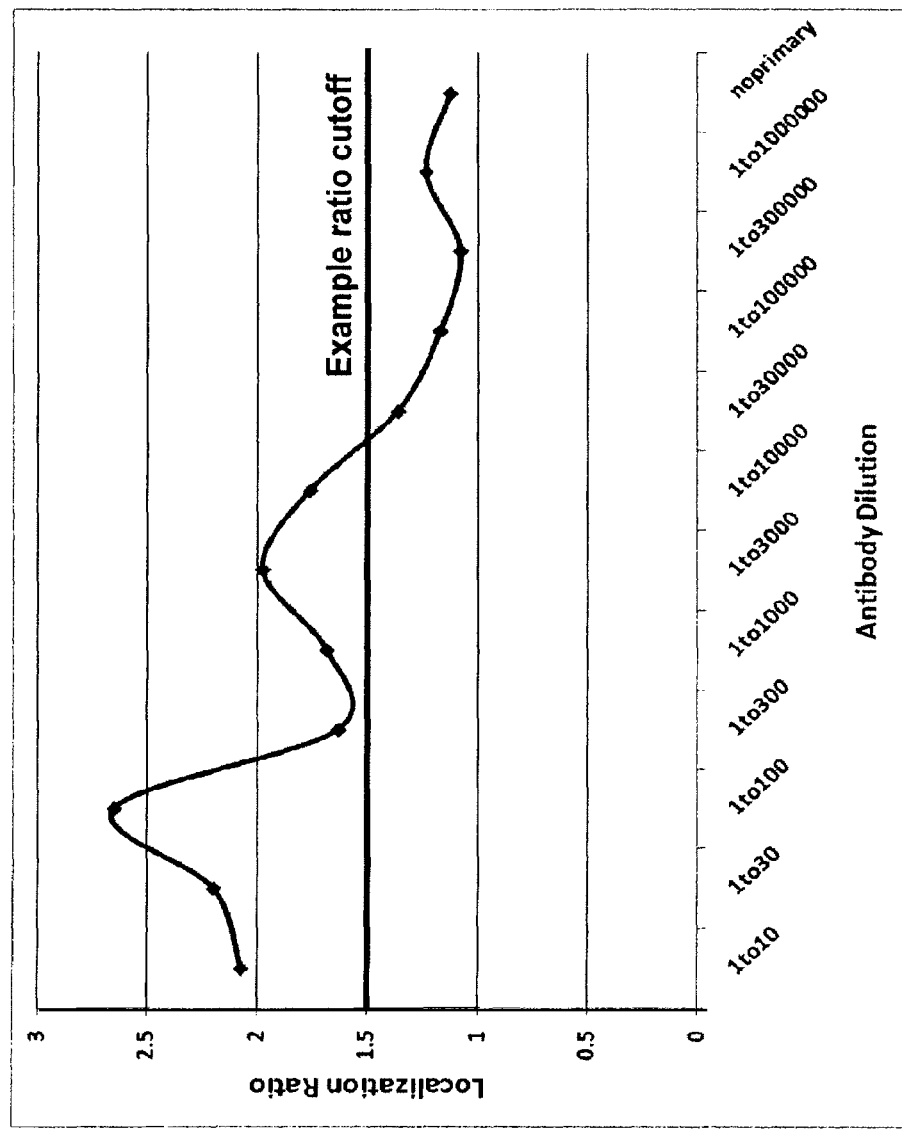
FIG. 20 is a graph illustrating exemplary average localization ratios.

As a separate measure of antibody specificity, if marker localization is known, localization evaluation can be performed whereby average localization ratios can be calculated for each antibody titer. An example is given in FIG. 20 for estrogen receptor (known to localize to the nucleus) whereby the average nuclear-to-cytoplasmic ratios over all samples for each specific titer are graphed. Because, localization within tissue is not an ideal metric for specificity, these data are used as a qualitative measure only in that if that measure for any given titer falls below an a priori determined cutoff value, such as 1.5. For any titers in which the localization ratio falls below such a threshold, the use of a different antibody or antibody conditions can be considered. The impetus would be that a different antibody or antibody conditions may produce localization ratios above the ratio cutoff value.

The protocol 400 then proceeds with quantitative data generation, which includes one or more of generation of data files for single image data calculations containing relative pixel intensities (parameter 1) at step 430 and data files for population/cohort-based calculations containing i.e. AQUA® scores (parameter 2) at step 435.

Note on Parameter 1

Measurements of central tendency and dynamic range can be performed either on an image-by-image basis (sample-by-sample) or as a pixel amalgam of all images within a given titer. If done on an image-by-image basis, % CV and swing ratios can be averaged for all samples within a titer to provide single representative values for the titer. If done by amalgam, the % CV and swing ratio are determined as single value as though performed for a single image. Measurement of a central tendency, such as a mean, standard deviation, and/or % CV, is performed at step 445. Measurement of a dynamic range is performed at step 450. The results can be combined at step 455.

Results

Once each metric as been determined for each parameter at steps 445 and 450, the metrics can be combined to provide a single "titer metric" for each titer. Because larger values for each metric correlate with a more optimal titer, the metrics can be combined together. For example, the metrics can be combined by multiplication and addition in the following fashion:

TITER METRIC: (% $CV_{P1}$*$SwingRatio_{P1}$)+(% $CV_{P2}$*$SwingRatio_{P2}$)

Where P1 and P2 represent Parameter 1 and Parameter 2 respectively.

The antibody dilution that provides the greatest resulting titer metric (at step 455) can be chose as the optimal titer.

EXAMPLES

Using only Parameter 2 metrics, optimal titers have been determined for the biomarkers estrogen receptor (ER), ERCC1, mTOR, and HER2, which represent two nuclear markers (ER and ERCC1) and two cytoplasmic/membrane markers (mTOR and HER2).

Figure 21A:
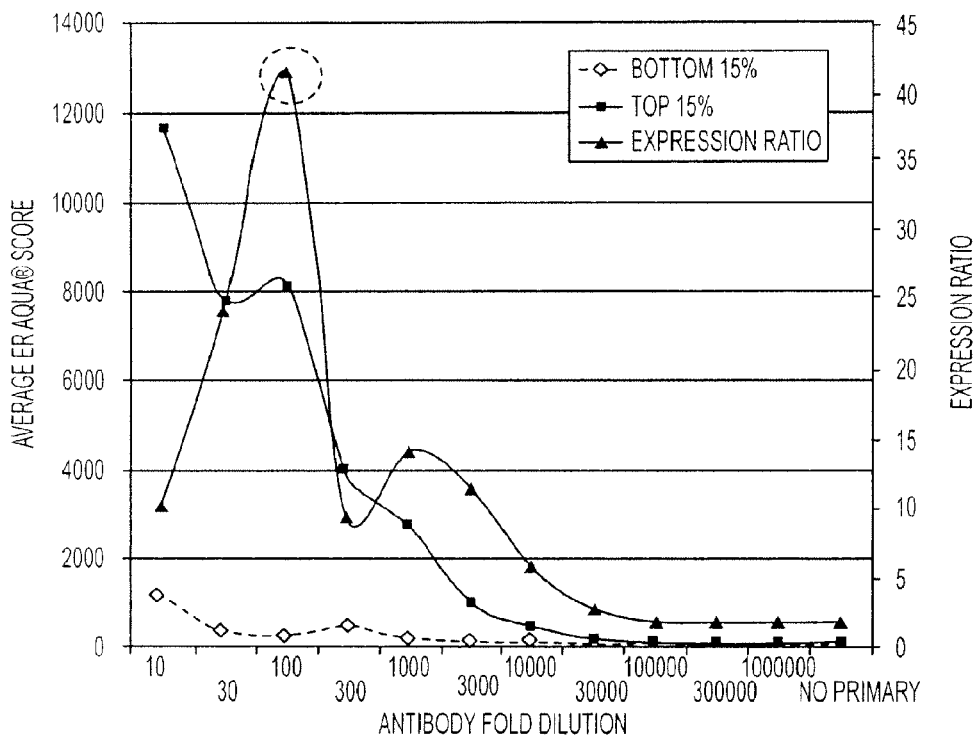
FIG. 21A through FIG. 21D each illustrate exemplary swing ratios determined according to an embodiment of the present invention.
Figure 21B:
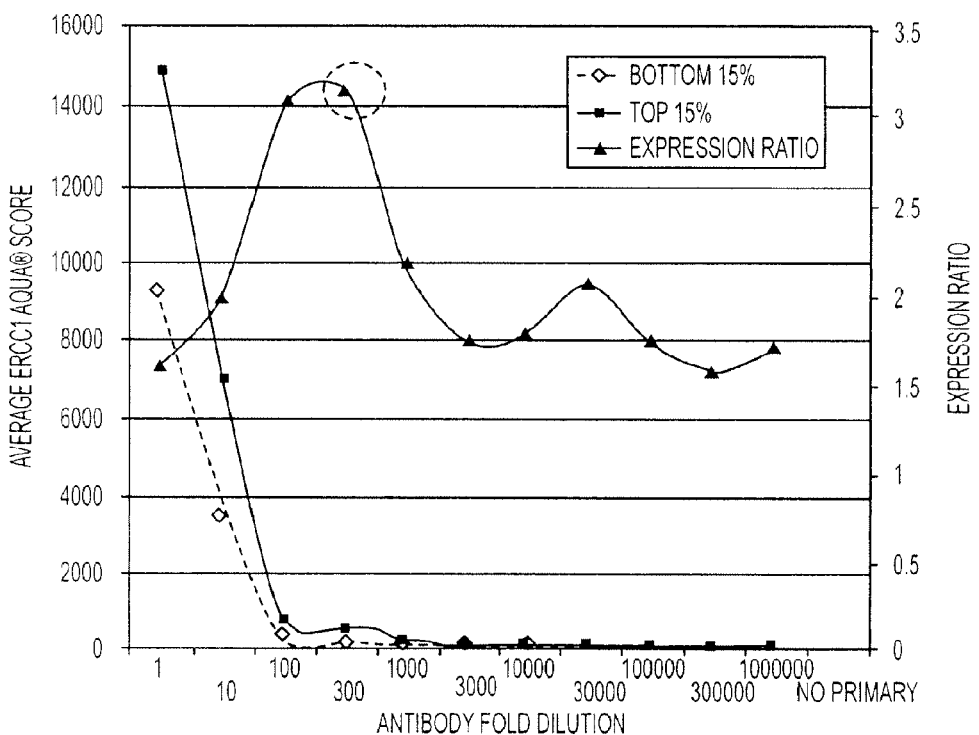
Figure 21C:
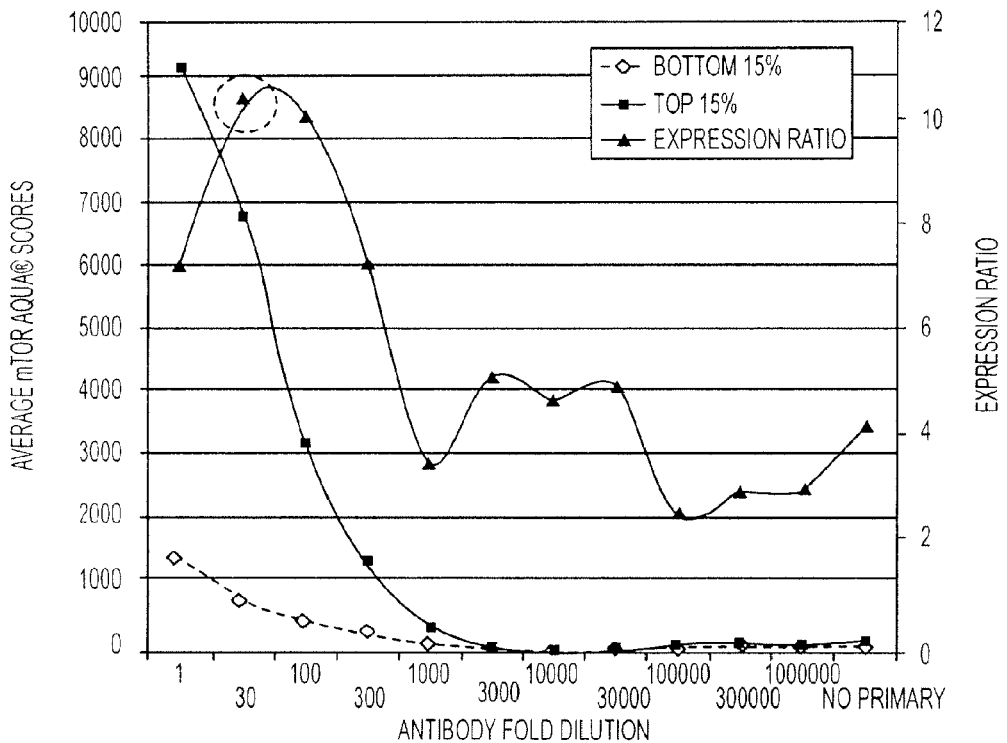
Figure 21D:
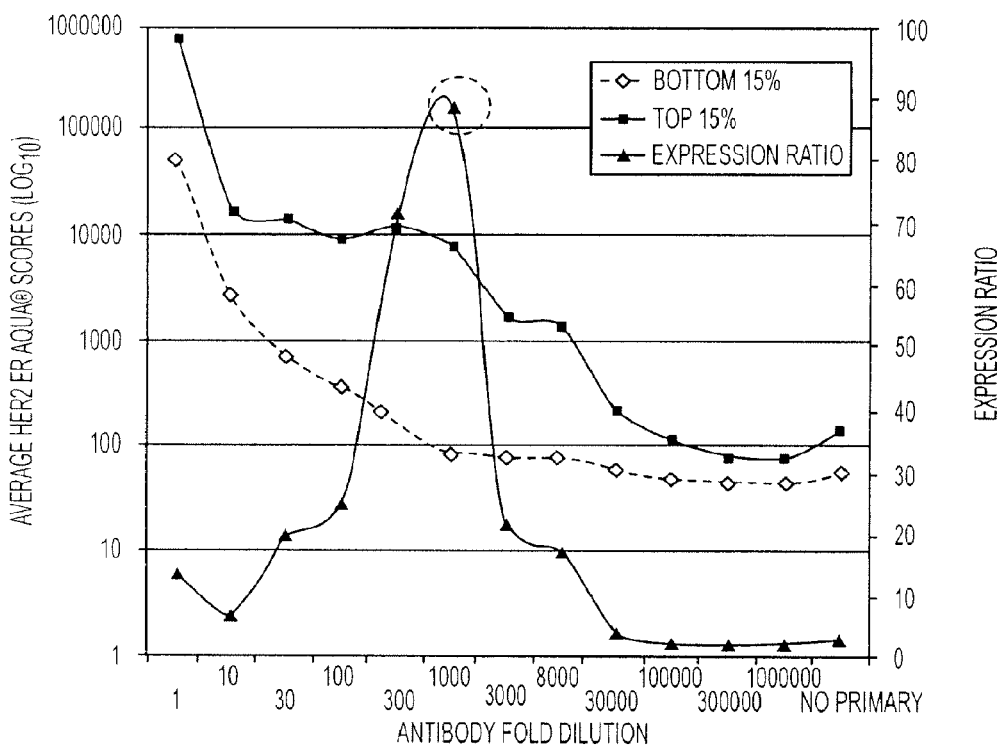
Figure 22A:
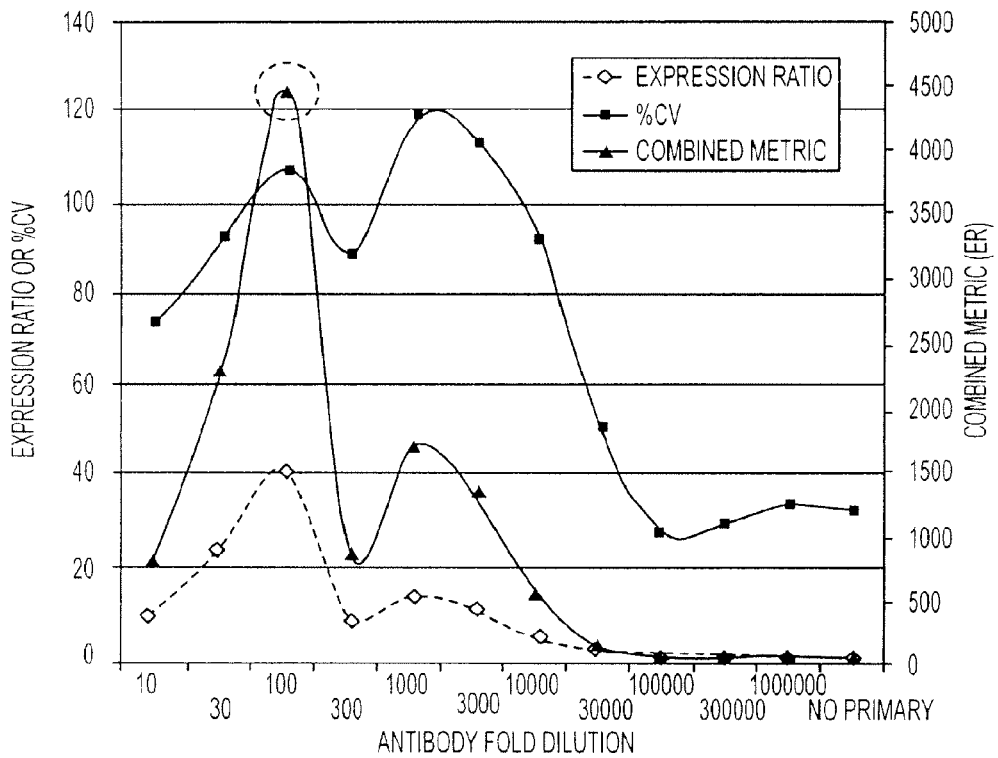
FIG. 22A through FIG. 22D each illustrate a exemplary swing ratios and % CV as a function of various metrics determined according to an embodiment of the present invention.
Figure 22B:
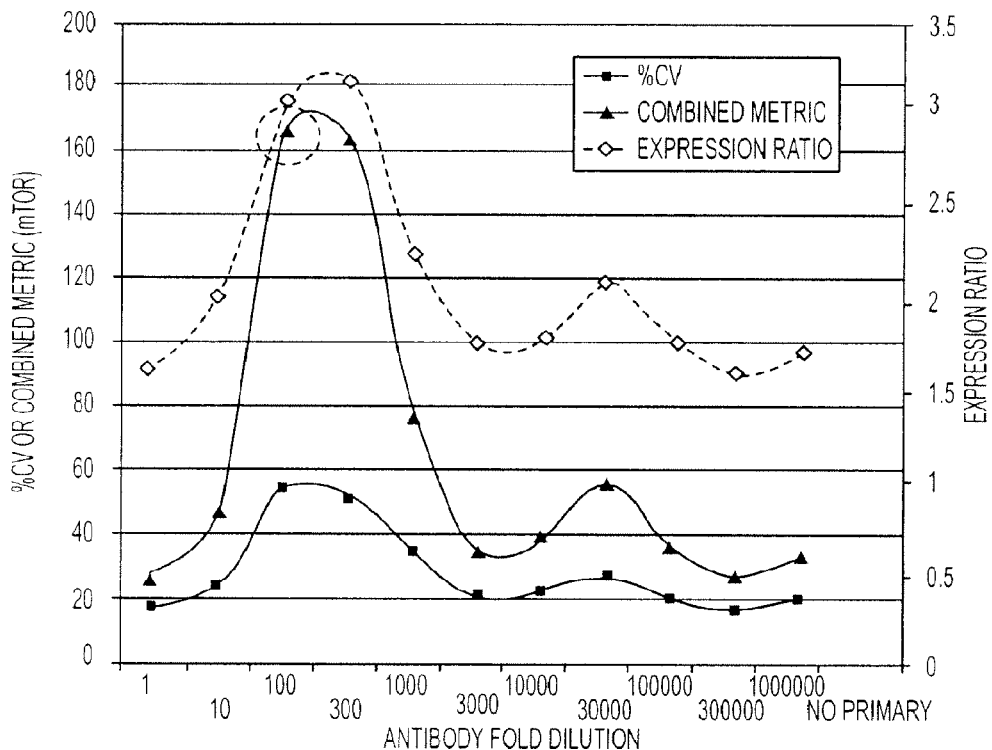
Figure 22C:
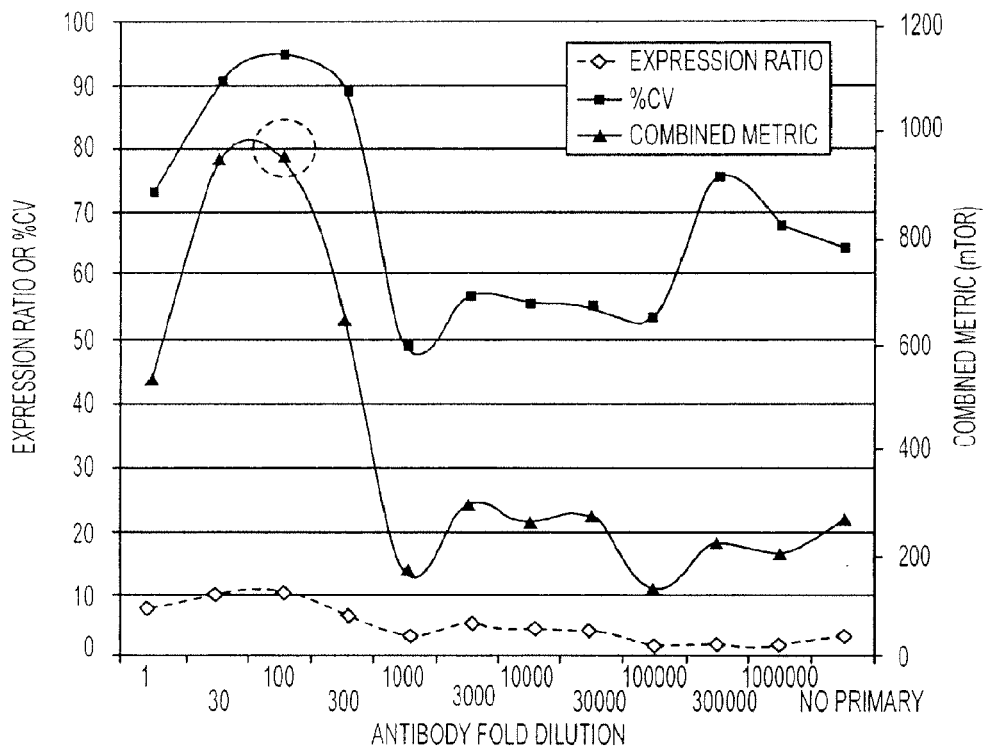
Figure 22D:
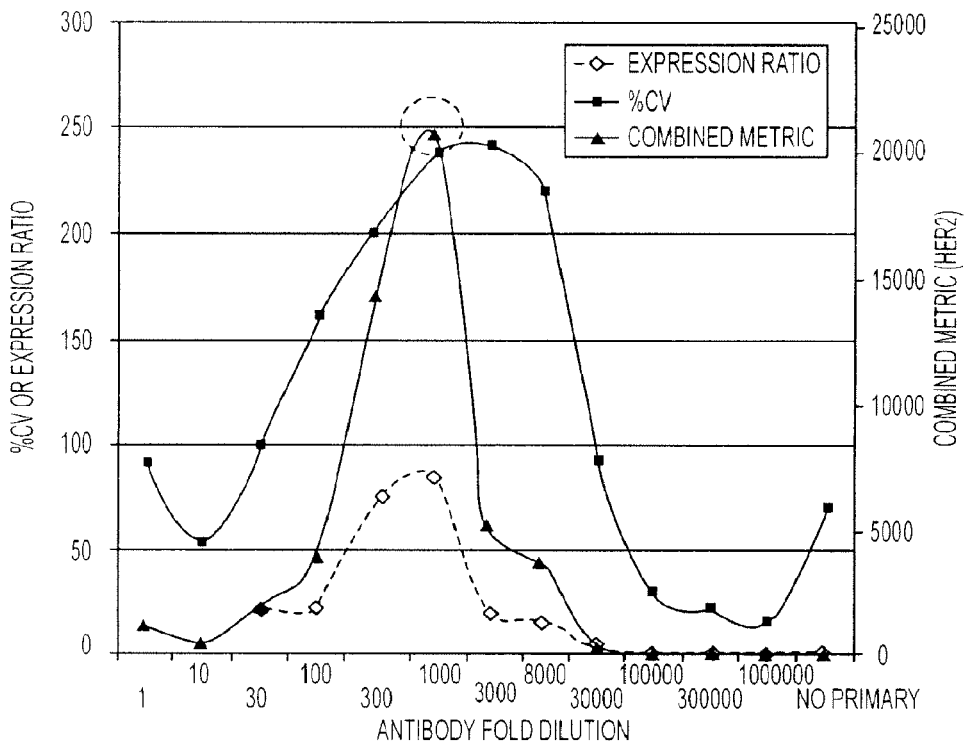

Represented in FIGS. 21A through 21D are the indicated expression, or swing ratios graphed as function of antibody fold dilution, including: anti-ER antibody (FIG. 21A), anti-RCC1 antibody (FIG. 21B); anti-mTOR antibody (FIG. 21C); and anti-HER2 antibody (FIG. 21D). Also shown are indicated top and bottom 15% average AQUA® scores.

Represented in FIGS. 22A through 22D are the indicated expression, or swing ratios and % CVs as a function of antibody fold dilution for the same markers as above. Also graphed is the combined metric (% $CV_{P2}$*$SwingRatio_{P2}$).

As indicated, the optimal dilution (as a function of only Parameter 2) for each marker antibody is 1:100 (ER); 1:100 (ERCC1); 1:100 (mTOR); and 1:1000 (HER2).

Various embodiments of methods and systems for determining an optimal dilution of a reagent have been described herein. The embodiments are given by way of example and are not intended to limit the scope of the present invention. It should be appreciated, moreover, that the various features of the embodiments that have been described may be combined in various ways to produce numerous additional embodiments. For example, in some embodiments, the system may allow certain metrics to be determined manually, while other metrics may not be available for review. Furthermore, the order in which metrics are processed and/or options for manual review provided is flexible.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for identifying an optimal antibody titer for an immunoassay comprising:
   receiving pixelized images of a plurality of tissue sample sets, each tissue sample set comprising a plurality of different tissue samples each harboring a concentration of an analyte and each stained with a respective antibody titer dilution for detection of the analyte concentration, different tissue sample sets having different respective antibody titer dilutions;
   performing a quantitative analysis of the pixelized images of the plurality of tissue sample sets, resulting in a respective selectivity value indicative of a staining intensity of each of the different tissue samples of each of the plurality of tissue sample sets;
   determining from pixel intensities of the pixelized images of each of the different tissue samples of each of the plurality of tissue sample sets, a respective sensitivity value, and for each tissue sample set of the plurality of tissue sample sets, a dynamic range for the analyte concentration; and
   identifying from the respective selectivity values and the respective sensitivity values of each of the different tissue samples of each of the plurality of tissue sample sets, an optimal antibody titer dilution that provides for an optimal dynamic range across all of the different tissue samples.

2. The method of claim 1, further comprising validating the received pixelized image, such that only valid images are included in identification of the optimal antibody titer dilution.

3. The method of claim 2, wherein the act of validating comprises performing a quantitative analysis of each the received pixelized images, only those pixelized images meeting a predetermined quality threshold being included in identification of the optimal antibody titer dilution.

4. The method of claim 1, wherein the act of performing a quantitative analysis comprises determining an automated subcellular localization and quantification score as a respective selectivity value indicative of the staining intensity of each of the different tissue samples of each of the plurality of tissue sample sets.

5. The method of claim 1, wherein the act of performing a quantitative analysis further comprising determining for each respective tissue sample of the plurality of tissue samples a localization ratio relating a first numeric value indicative of a staining intensity of a preferred sub-cellular compartment to a second numeric value indicative of a staining intensity of a non-preferred sub-cellular compartment, the preferred sub-cellular compartment being identified by a known marker localization.

6. A system for identifying an optimal antibody titer for an immunoassay comprising:
   a computer readable memory configured to receive pixelized images of a plurality of tissue sample sets, each tissue sample set comprising a plurality of different tissue samples each harboring a concentration of an analyte and each stained with respective antibody titer dilution for detection of the analyte concentration, different tissue sample sets having different antibody titer dilutions;
   an image processor in communication with the computer readable memory, the image processor configured to perform: a quantitative analysis of the pixelized images of the plurality of tissue sample sets, resulting in a respective selectivity value indicative of a staining intensity of each of the different tissue samples of each of the plurality of tissue sample sets;
   a determination from pixel intensities of the pixelized images of each of the different tissue samples of each of the plurality of tissue sample sets, a respective sensitivity value, and for each tissue sample set of the plurality of tissue sample sets, a dynamic range for the analyte concentration; and
   an identification from the respective selectivity values and the respective sensitivity values of each of the different tissue samples of each of the plurality of tissue sample sets, an optimal antibody titer dilution that provides for an optimal dynamic range across all of the different tissue samples.

7. The system of claim 6, further comprising a validation processor configured to validate the received pixelized images, such that only valid images are included in identification of the optimal antibody titer dilution.

8. The system of claim 7, wherein validation comprises performing a quantitative analysis of each the received pixelized images, those pixelized images meeting a predetermined quality threshold being included in identification of the optimal antibody titer dilution.

9. The system of claim 6, wherein the quantitative analysis comprises determining an automated subcellular localization and quantification score as a respective selectivity value indicative of the staining intensity of each of the different tissue samples of each of the plurality of tissue sample sets.

10. A non-transitory computer readable medium having the computer readable instructions stored thereon for execution by a processor to perform a quantitative process for identifying an optimal antibody titer for an immunoassay, the process comprising:

receiving pixelized images of a plurality of tissue sample sets, each tissue sample set comprising a plurality of different tissue samples each harboring a concentration of an analyte and each stained with a respective antibody titer dilution for detection of the analyte concentration, different tissue sample sets having different respective antibody titer dilutions;

performing a quantitative analysis of the pixelized images of the plurality of tissue sample sets, resulting in a respective selectivity value indicative of a staining intensity of each of the different tissue samples of each of the plurality of tissue sample sets;

determining from pixel intensities of the pixelized images of each of the different tissue samples of each of the plurality of tissue sample sets, a respective sensitivity value, and for each tissue sample set of the plurality of tissue sample sets, a dynamic range for the analyte concentration; and identifying from the respective selectivity values and the respective sensitivity values of each of the different tissue samples of each of the plurality of tissue sample sets, an optimal antibody titer dilution that provides for an optimal dynamic range across all of the different tissue samples.

11. A system for identifying an optimal antibody titer for an immunoassay comprising:

means for receiving pixelized images of a plurality of tissue sample sets, each tissue sample set comprising a plurality of different tissue samples each harboring a concentration of an analyte and each stained with a common antibody titer dilution for detection of the analyte concentration, different tissue sample sets having different common antibody titer dilutions;

means for performing a quantitative analysis of the pixelized images of the plurality of the tissue sample sets, resulting in a respective selectivity value indicative of a staining intensity of each of the different tissue samples of each of the plurality of tissue sample sets;

means for determining from pixel intensity information obtained from the pixelized images of each of the different tissue samples of each of the plurality of tissue sample sets, a respective sensitivity value, and for each tissue sample set of the plurality of tissue sample sets, a dynamic range for the analyte concentration; and means for identifying from the respective selectivity values and the respective sensitivity values of each of the different tissue samples of each of the tissue samples sets, an optimal antibody titer dilution that provides for an optimal dynamic range across all of the different tissue samples.

* * * * *